US010207121B2

(12) United States Patent
Guardiani et al.

(10) Patent No.: US 10,207,121 B2
(45) Date of Patent: Feb. 19, 2019

(54) ELECTRONIC MEDICAL SYSTEM WITH IMPLANTABLE MEDICAL DEVICE, HAVING WIRELESS POWER SUPPLY TRANSFER

(71) Applicant: ADO Holding SA, Lugano (CH)

(72) Inventors: Carlo Guardiani, Verona (IT); Daniele Piazza, Padova (IT); Paolo Menegoli, San Jose, CA (US); Leonardo Clementi, Milan (IT)

(*) Notice: Subject to any disclaimer, the term of this patent is extended or adjusted under 35 U.S.C. 154(b) by 0 days.

(21) Appl. No.: 15/336,196

(22) Filed: Oct. 27, 2016

(65) Prior Publication Data

US 2017/0043170 A1    Feb. 16, 2017

Related U.S. Application Data

(62) Division of application No. 13/948,538, filed on Jul. 23, 2013, now Pat. No. 9,504,842.

(51) Int. Cl.

| | |
|---|---|
| *A61N 1/00* | (2006.01) |
| *A61N 1/378* | (2006.01) |
| *H02J 17/00* | (2006.01) |
| *H04B 5/00* | (2006.01) |
| *H02J 50/20* | (2016.01) |
| *A61N 1/372* | (2006.01) |
| *A61M 5/142* | (2006.01) |
| *A61M 5/172* | (2006.01) |

(Continued)

(52) U.S. Cl.
CPC ....... *A61N 1/3787* (2013.01); *A61M 5/14276* (2013.01); *A61M 5/172* (2013.01); *A61N 1/37223* (2013.01); *H02J 17/00* (2013.01); *H02J 50/20* (2016.02); *H02J 50/27* (2016.02); *H02J 50/80* (2016.02); *H04B 5/0037* (2013.01); *A61M 2205/3515* (2013.01)

(58) Field of Classification Search
CPC ............ A61N 1/37223; A61N 1/37217; A61N 1/37211
USPC ........................................... 607/60
See application file for complete search history.

(56) References Cited

U.S. PATENT DOCUMENTS

| | | |
|---|---|---|
| 8,115,448 B2 | 2/2012 | John |
| 2006/0195162 A1 | 8/2006 | Arx et al. |

(Continued)

*Primary Examiner* — Amanda K Hulbert
*Assistant Examiner* — Philip C Edwards
(74) *Attorney, Agent, or Firm* — Thomas|Horstemeyer, LLP

(57) ABSTRACT

An electronic medical system is described. The system comprises an external RF power transmitter configured to emit a first power signal via an electromagnetic coupling, said RF power transmitter being configured to emit said first energy signal with a power no greater than 1W. The system further comprises an implantable medical device comprising: at least one receiver antenna configured to receive said first energy signal via an electromagnetic coupling; an RF power receiver module configured to extract a second energy signal having a power of at least 1 mW and to be powered by said second energy signal; a power actuator module, operatively connected to the RF power receiver module, powered by said second energy signal. The power actuator module is configured to deliver a medical treatment to at least a target tissue of a patient on the basis of a control signal generated by the RF power receiver module.

11 Claims, 23 Drawing Sheets

(51) Int. Cl.
*H02J 50/80* (2016.01)
*H02J 50/27* (2016.01)

(56) References Cited

U.S. PATENT DOCUMENTS

| | | | |
|---|---|---|---|
| 2008/0183247 A1* | 7/2008 | Harding | A61N 1/0563 607/60 |
| 2009/0204170 A1* | 8/2009 | Hastings | A61N 1/0565 607/33 |
| 2015/0032052 A1 | 1/2015 | Guardiani et al. | |

* cited by examiner

ELECTRONIC MEDICAL SYSTEM WITH IMPLANTABLE MEDICAL DEVICE, HAVING WIRELESS POWER SUPPLY TRANSFER

CROSS-REFERENCE TO RELATED APPLICATIONS

This application is a divisional application of U.S. Non-Provisional application entitled, "ELECTRONIC MEDICAL SYSTEM WITH IMPLANTABLE MEDICAL DEVICE, HAVING WIRELESS POWER SUPPLY TRANSFER," having Ser. No. 13/948,538, filed on Jul. 23, 2013, which is incorporated herein by reference in its entirety.

FIELD OF THE DISCLOSURE

The present disclosure relates generally to the field of human body medical treatment system with implantable medical devices, particularly, to an electronic medical system with implantable medical device, having wireless power supply transfer.

BACKGROUND

In recent years, medical treatment of the human body (e.g. electrical stimulation of various tissues or organs, delivering of medical substances into tissues or organs, and so on) has been increasingly used to treat a number of different medical conditions such as for example chronic pain disorder, alcohol and drug dependence, and other pathological conditions.

In the case of electrical stimulation, while a few of these treatments are applied by using external devices and electrodes, the majority and the most relevant of these techniques involves implanting electrodes and often the entire stimulating device in the human body.

Several commercial implantable devices have been manufactured and successfully applied and they are becoming increasingly adopted.

A typical electronic medical system for electrical stimulation includes an implantable medical device having one or more electrodes delivering electrical stimulus to a specific tissue or organ in the form of an electrical current or voltage signals.

Furthermore, the implantable medical device includes a control unit that is configured to modulate and provide an appropriate sequence of stimuli (typically, a periodic sequence of electrical voltage or current impulses), wherein the frequency, duty cycle and amplitude of the electrical signal can be adaptively varied in order to maximize the effectiveness of the treatment for each individual patient.

In addition, the implantable medical device typically includes a conductive element (e.g. a catheter) connecting the control unit to the electrodes, and an energy storage element providing the power supply to the control unit, usually in the form of an electro-chemical storage device, or a battery.

The electronic medical system having said implantable medical device has several limitations.

First of all, the control unit and energy storage element (battery) are usually integrated and occupy a relatively sizeable volume. Furthermore, both the control unit and the battery need to be suitably protected by inserting them into a rigid metallic case coated in biocompatible materials, and then implanted in a suitable anatomical cavity, in most cases disposed relatively far away from the tissue or the organ to be medically treated (e.g. electrically stimulated).

For this reason, a routing of a relatively long catheter from the control unit to the electrodes, thus increasing post-surgery patient discomfort and the probability of infections, is needed.

Moreover, the implantation of the medical treatment system typically requires at least two different surgeries on the patient.

In a first surgery, the electrodes are accurately placed in the target position (tissue or organ) into the human body, while the control unit and the battery are kept external and are connected to one another through a catheter. This is required to test the patient's reaction to the medical treatment procedure and eventually to adjust, to optimize and to fine tune the parameters of the electrical stimulus. Once the effectiveness of the medical treatment procedure has been tested, a second surgery is performed on the patient to implant the control unit in the target location. Obviously, performing two subsequent surgeries represents a inconvenience for the patient.

Furthermore, a number of disadvantages arise from the presence of an electrochemical energy storage element (battery), e.g. the limited battery's lifetime which implies the need of its replacement by surgery, the impossibility of performing Magnetic Resonant Imaging (MRI) test, the presence of heavy metals and other potentially hazardous material, such as mercury, cadmium, nickel, and lithium, requiring extra care for disposal avoiding leakage.

SUMMARY OF THE INVENTION

According to some aspects of the present description, an electronic medical system with wireless power supply transfer is provided which overcomes the drawbacks above mentioned with reference to the cited prior art.

According to a first embodiment, there is provided a electronic medical system comprises an external RF power transmitter configured to emit a first power signal via an electromagnetic coupling, said RF power transmitter being configured to emit said first energy signal with a power no greater than 1 W. The system further comprises an implantable medical device comprising: at least one receiver antenna configured to receive said first energy signal via an electromagnetic coupling; an RF power receiver module operatively connected to the at least one receiver antenna, the RF power module being configured to extract a second energy signal having a power of at least 1 mW, the RF power receiver module being powered by said second energy signal, the RF power receiver module being configured to generate a control signal; a power actuator module, operatively connected to the RF power receiver module, powered by said second energy signal, the power actuator module being configured to receive said control signal, the power actuator module being configured to deliver a medical treatment to at least a target tissue of a patient on the basis of said control signal; wherein the implantable medical device comprises a RF front end module, an impedance matching network, a voltage rectifier, the power actuator module and a voltage protection and backscattering module.

Further aspects are provided in the description, drawings and claims of the present application.

BRIEF DESCRIPTION OF THE DRAWINGS

Further features and advantages of the system according to the present disclosure will appear more clearly from the following description of preferred embodiments thereof, given by way of a non-limiting example with reference to the annexed figures, wherein.

DETAILED DESCRIPTION OF THE PREFERRED EMBODIMENTS

With reference to the block diagram of FIG. 1, an electronic medical system 100 with wireless power supply transfer, hereinafter also referred to simply as system 100, is now described.

The system 100 comprises an external RF (Radio Frequency) power transmitter 101 configured to communicate and transfer RF energy via a wireless transfer, i.e. an electromagnetic coupling in the far field region.

The external RF power transmitter 101 may be worn by or carried by a patient as a portable device or may be positioned near the patient.

In greater detail, the external RF power transmitter 101 is configured to emit a first energy signal S1 via an electromagnetic coupling. In order to meet regulatory and safety constraints, the external RF power transmitter 101 is advantageously configured to emit said first energy signal S1 having an instantaneous transmission power no greater than 1 W (30 dBm).

It should be observed that the above indicated value of 1 W corresponds to a value of Equivalent Isotropic Radiated Power (EIRP) of 30 dBm.

With reference again to FIG. 1, the system 100 further comprises an implantable medical device 102, configured to receive from the external RF power transmitter module 101 said first energy signal S1. As it will be described later, the implantable medical device 102 may be implanted under the skin of the patient.

Figure 1:
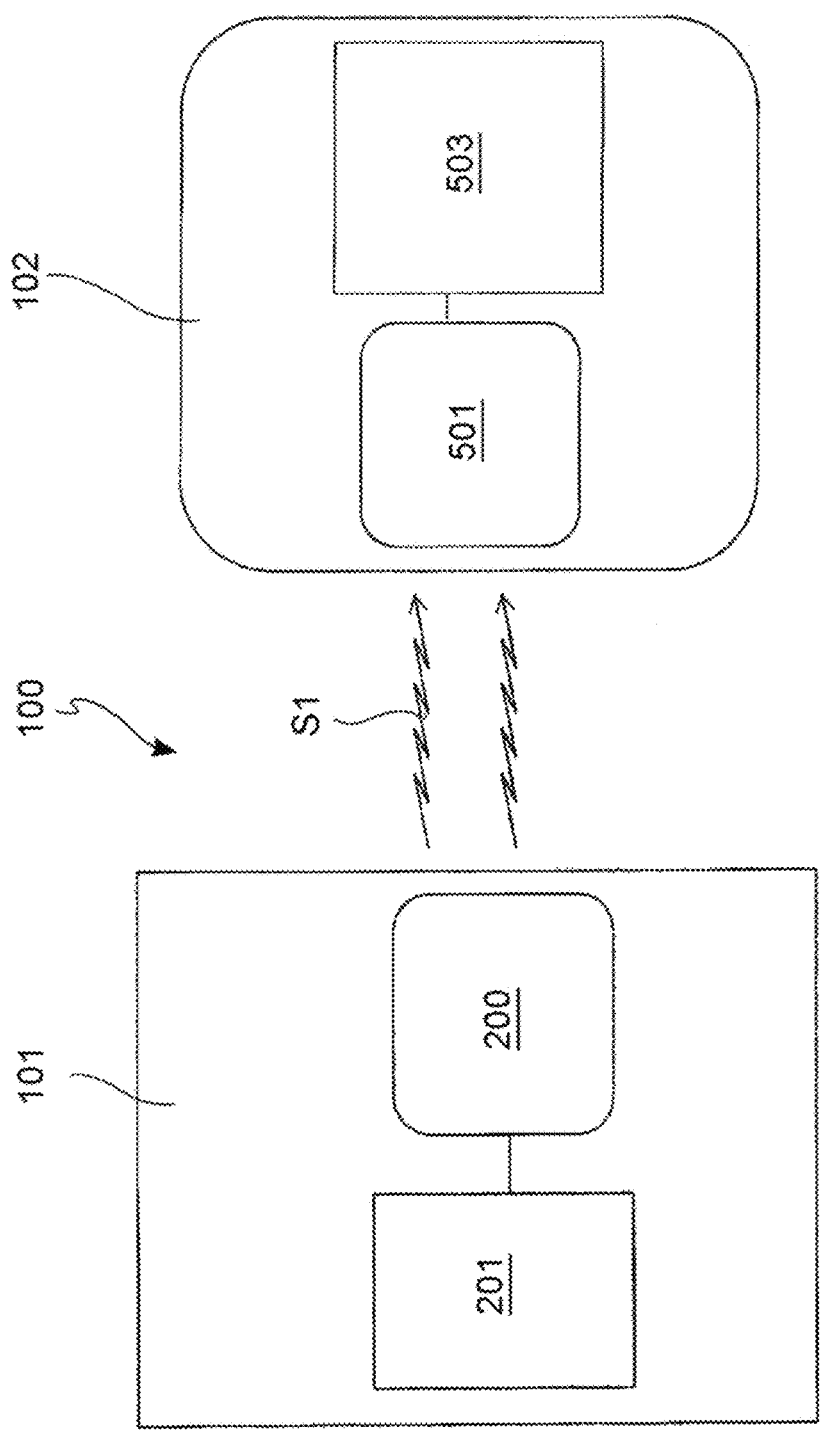
FIG. 1 shows a block diagram of a medical treatment system with wireless power supply transfer according to an embodiment of the disclosure.
Figure 2:
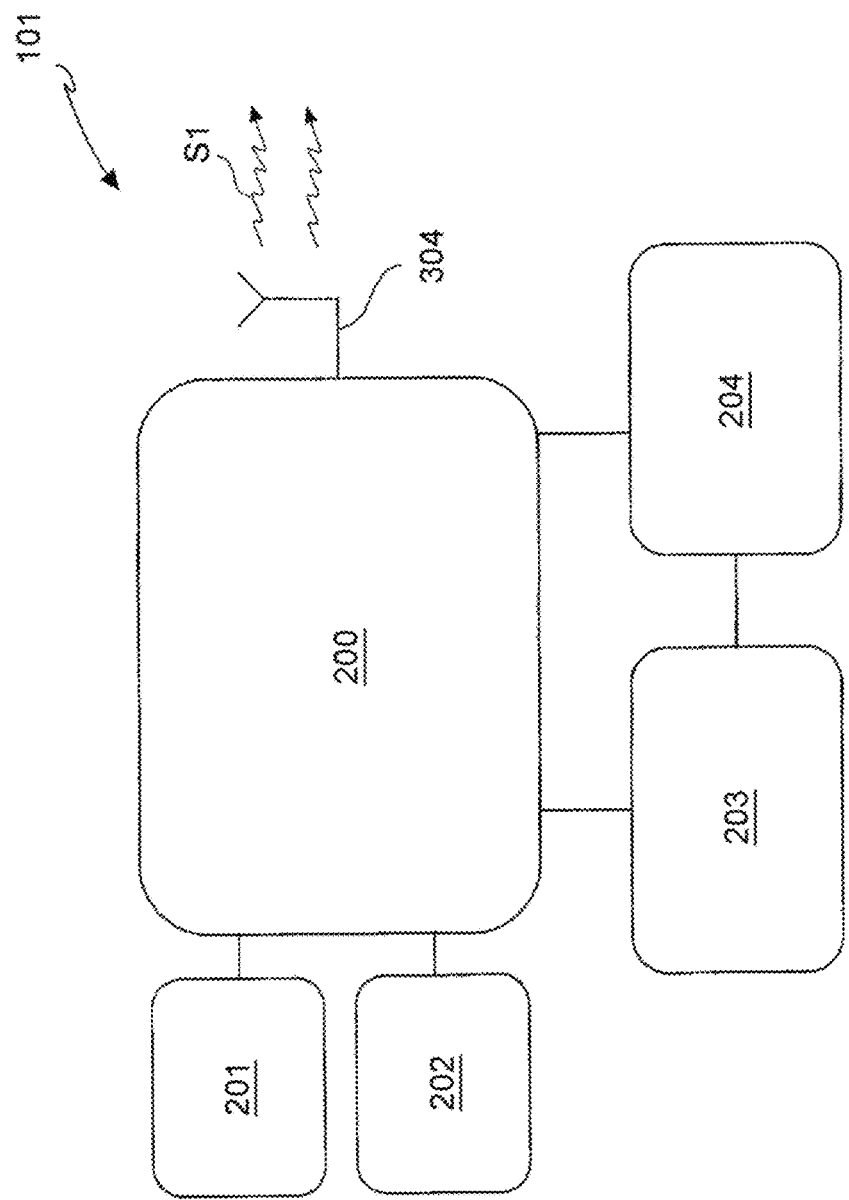
FIG. 2 shows a block diagram of a first portion of the system of FIG. 1.

With reference now to FIG. 1 and FIG. 2, the external RF power transmitter 101, hereinafter also simply transmitter 101, comprises a RF power transmitter module 200.

The transmitter 101 further comprises an energy storage element 201, e.g. a battery or a rechargeable battery, operatively connected to the RF power transmitter module 200. The energy storage element 201 is configured to transmit power to the RF power transmitter module 200 and generally to the transmitter 101.

In addition, the transmitter 101 comprises a power limiter module 202 operatively connected to the RF power transmitter module 200. The power limiter module 202 is configured to limit the first energy signal S1 to an instantaneous transmission power no greater than 1 W.

It should be noted that the power limiter module 202 can be implemented in various way. An example of power limiter module 202 will be provided in the following.

The transmitter 101 further comprises a first communication interface module 203 operatively connected to the RF power transmitter module 200.

The first communication interface module 203 is configured to communicate data (transmit and receive) with the implantable medical device 102 via a wireless link (forward and reverse link), as it will be also explained later. The first communication interface module 203 comprising a coder and a decoder of the communication data, a modulator and other elements configured to performs the functions required to exchange data via the forward and the reverse link between the transmitter 101 and the implantable medical device 102. The first communication interface module is configured to operate with a low power wireless communication protocol such as, for example, Bluetooth 4.0, ANT and/or ANT+, Zigbee, and so on.

The transmitter 101 further comprises a first programmable control unit 204, i.e. a microprocessor or a microcontroller, configured to manage the transmitter 101. In fact, the first programmable control unit 204 is operatively connected to all the components of the transmitter 101.

Figure 3:
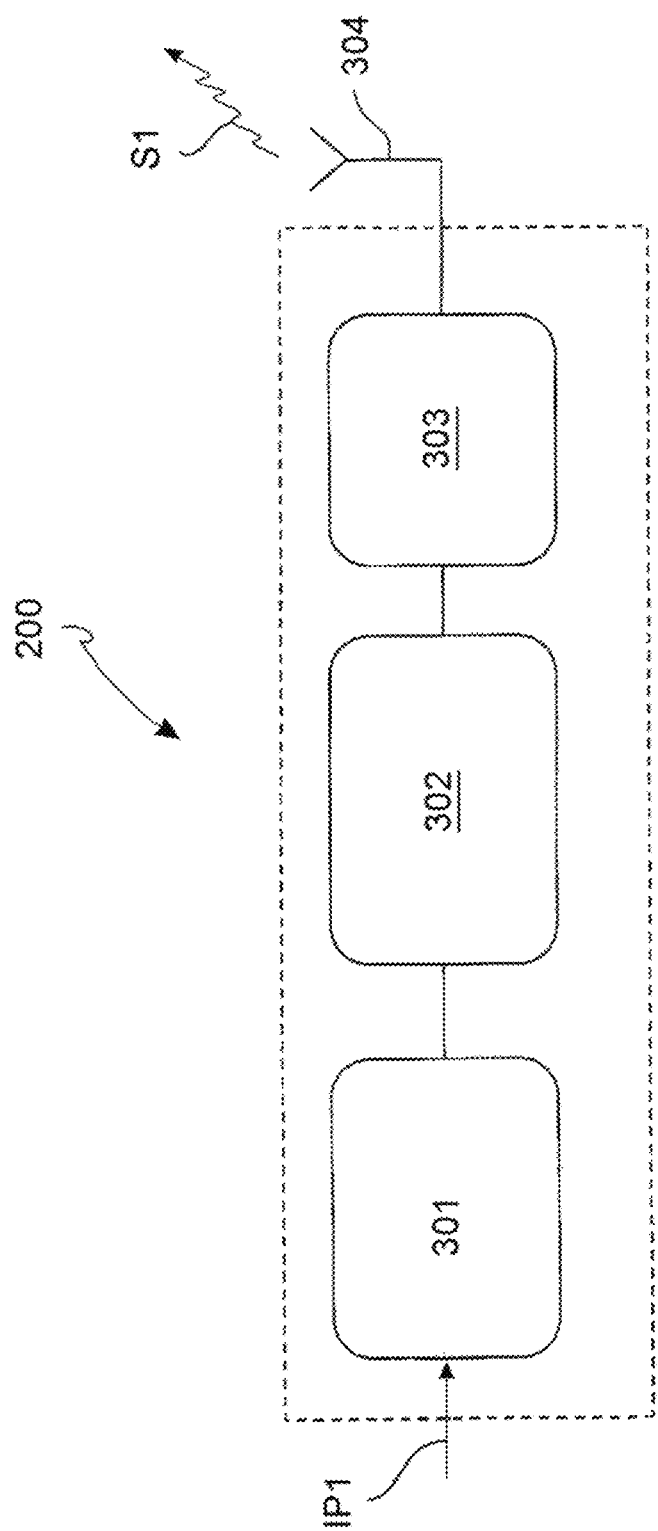
FIG. 3 shows a block diagram of a component of the first portion of the system of FIG. 2.

With reference now to the block diagram of FIG. 3, the RF power transmitter module 200 is now described.

The RF power transmitter module 200 comprises an RF power amplifier 301, an impedance matching module 302, a resonant network module 303 and a transmitter antenna 304 in cascade arrangement. Such an arrangement is configured to receive an input power IP from the battery 201 and to generate the first energy signal S1 having an instantaneous transmission power no greater than 1 W, to be emitted via the electromagnetic coupling to the implantable medical device 102, at a carrier frequency component preferably of 433.92 MHz.

In a greater detail, the RF power amplifier 301 is configured to generate an RF output signal with the required power level from a low power input, the impedance matching module 302 is configured to maximize the power to be transferred to the transmitter antenna 304, i.e. to minimize reflections of power into the RF power amplifier 301), the resonant network module 303 is configured to maximize the circuit Q, i.e. to increase the power to be transferred at the dominant frequency of operation with respect to the nearby frequencies (i.e. narrow-band).

Figure 4:
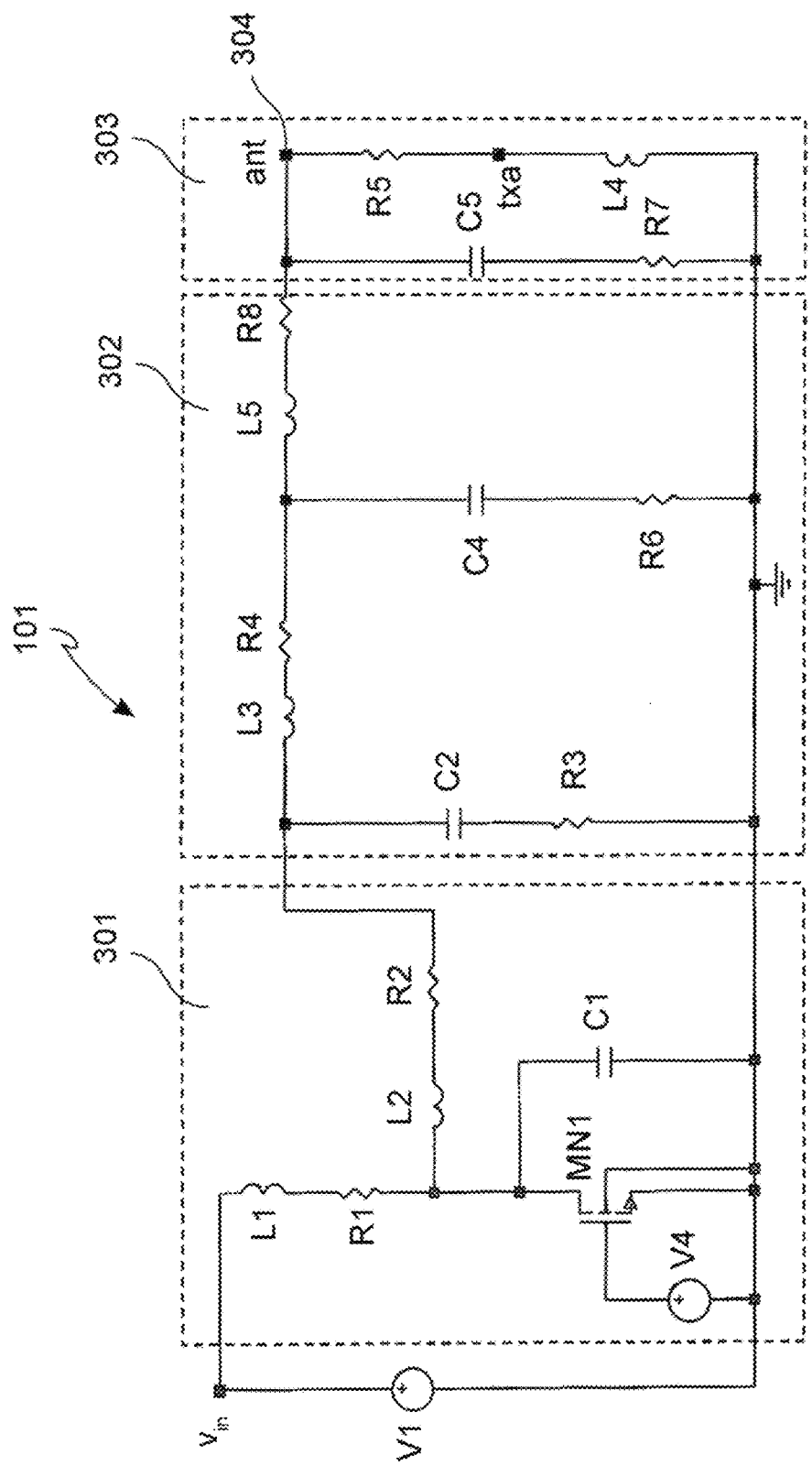
FIG. 4 shows with an electric circuit the component of FIG. 3 according to an embodiment of present disclosure.

With reference to FIG. 4, the transmitter 101 is represented by a circuital point of view in accordance with an embodiment of the present disclosure.

It should be noted that the electric component corresponding to the blocks of FIG. 2 or 3 are indicated with the same reference numbers or they are grouped within blocks with dotted lines indicated with the same reference numbers.

According to an embodiment of the present disclosure, the RF power amplifier 301 is a Class-E amplifier with Zero Voltage Switching. It should be noted that a Class-E amplifier, operating in soft switching, advantageously allows to guarantee high efficiency (ideally close to 100%) and low distortion.

According to another embodiment, the RF power amplifier 301 is configured to generate a second (H2) and a third (H3) harmonic components that are at least 70 dBc less than the carrier frequency component (433.92 MHz).

Figure 5:
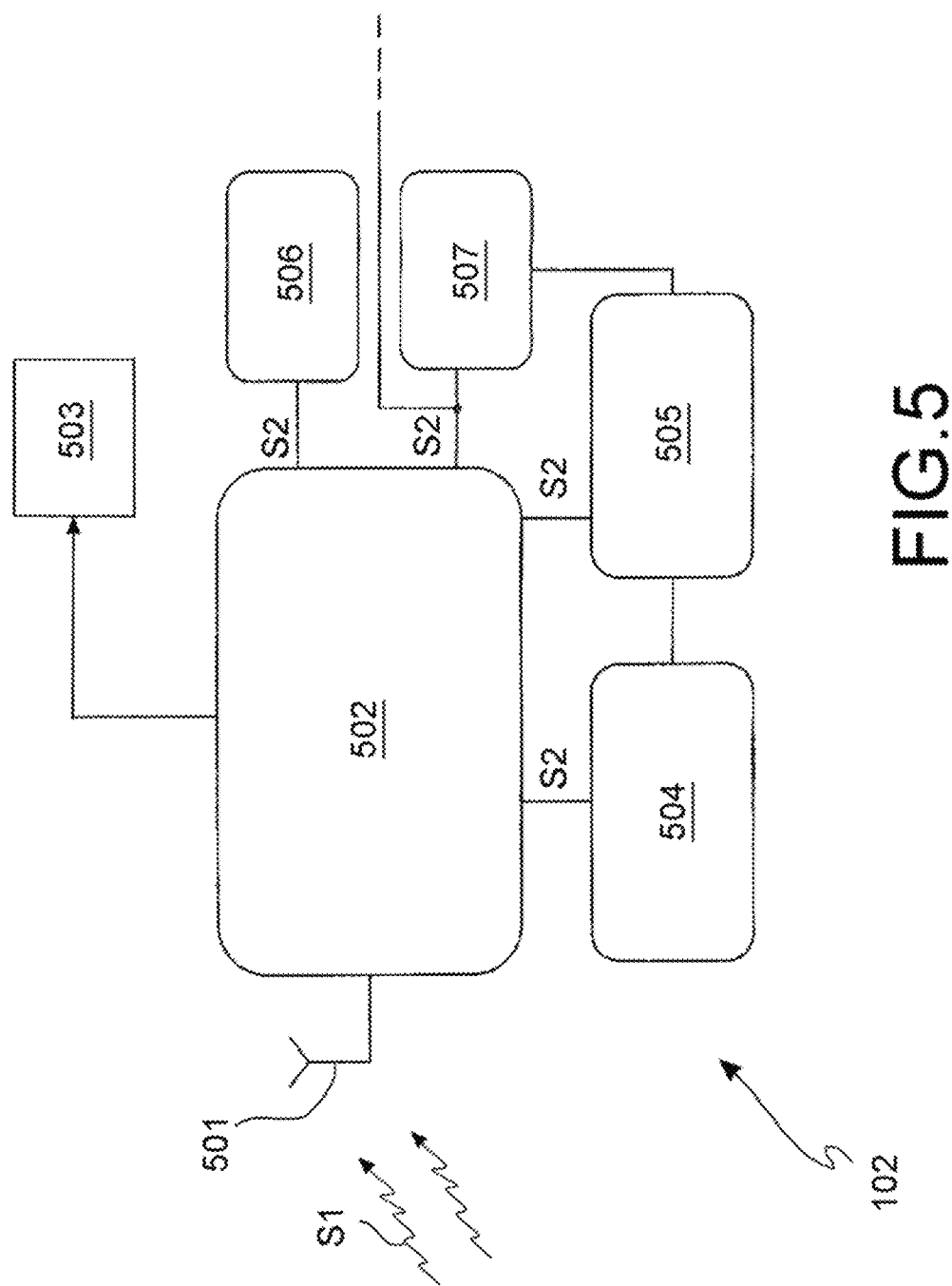
FIG. 5 shows with a block diagram a second portion of the system of FIG. 1.

With reference now to FIG. 1 and FIG. 5, the implantable medical device 102 comprises at least one receiver antenna 501 configured to receive said first energy signal S1 via an electromagnetic coupling, i.e. in the far field region.

The at least one receiver antenna 501 may be of the subcutaneous type.

In particular, the at least one subcutaneous antenna 504 can be placed on the target tissue or buried in the target tissue in order to minimize losses in the radiated signal, i.e. the first energy signal S1.

Figure 14A:
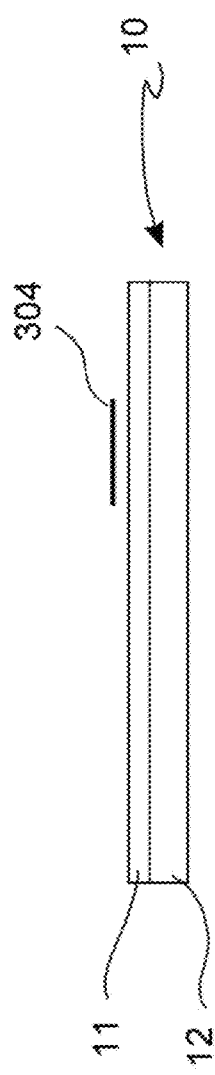
FIGS. 14a-14b illustrate a cross section view and a top view, respectively, of an arrangement of a component of the system of the present disclosure on a portion of a target tissue, according to an embodiment of the present disclosure.
Figure 14B:
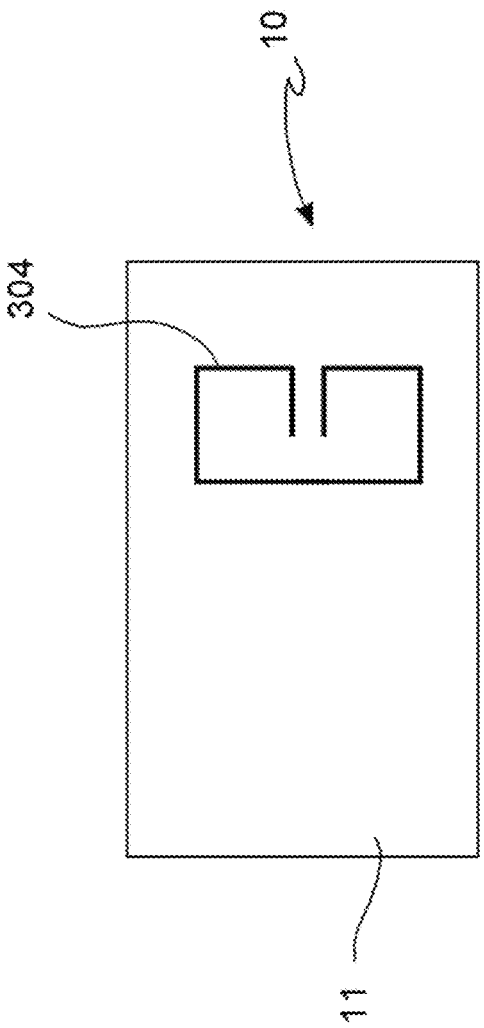

With reference to FIGS. 14a and 14b, the target tissue 10 comprises a skin layer 11 and a fat layer 12 (shown only in FIG. 14a). The transmitter antenna 304 of the external RF power transmitter 101 is arranged in proximity of the target tissue 10, above the skin layer 11.

As illustrated in the FIG. 14b, the transmitter antenna 304 of the external RF power transmitter 101 can be a metal folded dipole. In the same way, in an embodiment of the present disclosure, also the at least one subcutaneous antenna 501 may be a metal folded dipole.

Figure 15:
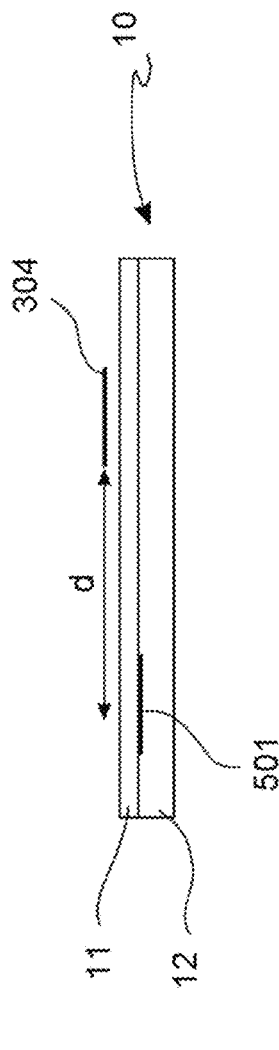
FIGS. 15, 16 and 17 illustrate top views of arrangements of components of the system of the present disclosure on a portion of a target tissue, in accordance with different embodiments of the present disclosure, respectively.

According to the embodiment of FIG. 15, the at least one subcutaneous receiver antenna 504 may be placed in the skin layer 11, e.g. immediately under the skin layer 11, of the target tissue 10. The at least one subcutaneous receiver antenna 504 is placed at a distance d from the transmitter antenna 304, e.g. at a frequency of 433.92 MHz.

Figure 16:
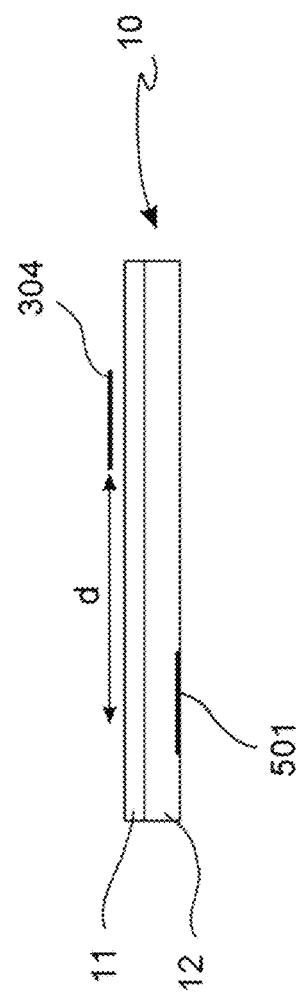

According to the embodiment of FIG. 16, the at least one subcutaneous receiver antenna 504 may be placed in the fat layer 12 of the target tissue 10. The at least one subcutaneous receiver antenna 504 is placed at a distance d from the transmitter antenna 304, e.g. at a frequency of 433.92 MHz. It should be observed that the lower conductivity of the fat layer 12 of the target tissue 10 allows to obtain losses lower than placing the at least one subcutaneous receiver antenna 501. Therefore, it is preferable to bury the at least one subcutaneous receiver antenna 501 in the fat layer 12 of the target tissue 10.

Figure 17:
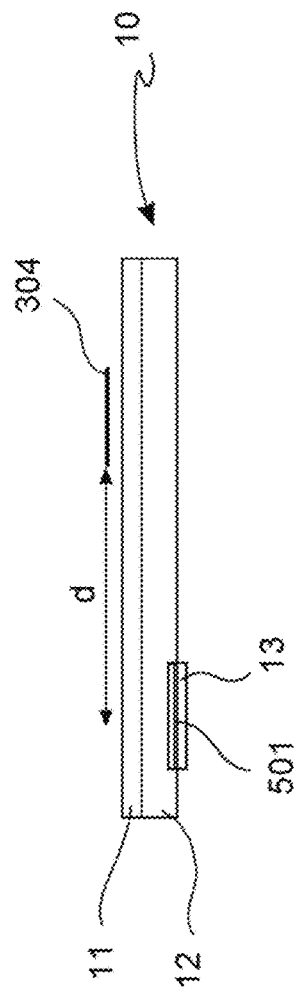

According to the embodiment of FIG. 17, the at least one subcutaneous receiver antenna 504 may be buried in the fat layer 12 of the target tissue 10. The at least one subcutaneous receiver antenna 504 is placed at a distance d from the transmitter antenna 304, e.g. at a frequency of 433.92 MHz. In this embodiment, the at least one subcutaneous receiver antenna 504 is coated in a bio-compatible material 13, e.g. silicone. Embedding the at least one subcutaneous receiver antenna 504 in the bio-compatible material advantageously improves the gain of the antenna.

According to an embodiment of the present disclosure, the bio-compatible material 13 can be a low electrical conductivity material, typically less than $10^{-10}$ S/m (e.g. glass is $10^{-11}$ S/m, rubber or plastic is $10^{-14}$ S/M or lower– $10^{-20}$ S/m), e.g. a polymer.

According to another embodiment, further improvement in the antenna gain can be achieved by using a secondary metallic strip coupled to the at least one subcutaneous receiver antenna 504 to maximize the gain in the direction of the metal strip or in the opposite direction depending on the length of the structure. This technique improves the antenna gain of ~3 dB increasing further the range.

In addition, in order to provide enough power at the RF power receiver module 502 for the system 100 to work properly, it is necessary to have the transmitter antenna 304 and the at least one subcutaneous receiver antenna 504 separated less than 30-35 cm. This can be valid specifically when using a directional antenna at the RF receiver power module.

In addition, it should be noted that also since any object that will be placed between the transmitter antenna 304 and the at least one subcutaneous receiver antenna 504 will negatively impact the path loss a clear line of sight is required between the two antennas.

According to another embodiment, in combination with any of the previous embodiment, the at least one subcutaneous antenna is printed on a flexible material, e.g. a conductive polymer antenna printed on plastic films.

Furthermore, according to another embodiment, in combination with any of the previous embodiment, the at least one subcutaneous receiver antenna 501 is an omnidirectional antenna.

According to an alternative embodiment, the at least one subcutaneous receiver antenna 501 is a directional antenna.

According to other embodiments, alternatively or in combination with the previously described embodiments, the at least one receiver antenna 104 may be a dipole antenna, a monopole antenna, a slot antenna, a patch antenna, or an antenna with another form factor configured to receive the first energy signal S1 via the electromagnetic coupling in the far field region.

With reference to the distance d between the transmitter antenna 304 and the at least one subcutaneous receiver antenna 504, to ensure the power transfer necessary for the implantable medical device 102 to work properly without battery, the loss introduced by the wireless link between the transmitter antenna 304 and the at least one subcutaneous receiver antenna 504 needs to be less than 25 dB.

If both the above indicated antennas are placed in the far field region, the ratio of the power received (Pr) over the power transmitted (Pt) can be estimated using the following equation:

$$Pt/Pr[dB]=Gt[dB]+Gr[dB]+20 \log 10[\lambda/4\pi d]$$

wherein Gt and Gr are the gain of the transmitter antenna 304 and the at least one subcutaneous receiver antenna 504, respectively; $\lambda$ is the wavelength in the free space and d is the distance between the above indicate antennas.

The higher the antenna gain at the RF power receiver module 502 and at the transmitter module 101 and the higher the maximum distance for which the communication/power transfer system performs properly, e.g. when the ratio Pr/Pt>−25 dB.

The requirement for having the system working for distance, d, greater than 20 cm determines to have the system operating at frequencies, f, in the ISM bands below 2 GHz. Considering also that the human tissue that surrounds the at least one subcutaneous receiver antenna 504 has a strong negative effect on Gr, in the order of ~15 dB of loss, it is proposed to adopt a frequency of operation below 500 MHz. For this reason, the selected frequency for the system can be 433.92 MHz (the highest frequency of the regulated ISM frequencies below 500 MHz), already previously introduced. It should be noted that the highest possible frequency below 500 MHz has been selected to advantageously allow the design of small antennas and small components of the system 100.

The path loss of the wireless link has been determined through electromagnetic simulations to determine the maximum distance at which the transmitter antenna 304 and the at least one subcutaneous receiver antenna 504 need to be placed. To this end the electromagnetic simulations have been conducted modeling the tissues of the head (target tissue) as a two layers material composed of a first layer of skin and a second layer of fat, as previously defined.

With reference again to FIG. 5, the implantable medical device 102 further comprises a RF power receiver module 502 operatively connected to the at least one receiver antenna 501.

The RF power receiver module 502 is configured to extract a second energy signal S2 having an instantaneous power of at least 1 mW, on the basis of said first energy signal S1.

In addition, the RF power receiver module 502 is configured to generate a control signal CS.

The implantable medical device 102 further comprises a power actuator module 503, operatively connected to the RF power receiver module 502, configured to receive said control signal CS.

In particular, the power actuator module 503 is configured to deliver a medical treatment to at least a target tissue of a patient on the basis of said control signal CS.

It should be noted that, according to a first embodiment of the present disclosure, the medical treatment is an electronic stimulation of the target tissue. In such first embodiment, the power actuator module 503 may include a pulse signal generator configured to apply electrical stimulation to the target tissue, controlled by means of the control signal CS, providing electrical stimuli to one or more electrodes operatively connected to the target tissue.

In particular, the one or more electrodes may be configured to be positioned in proximity to, or attached to, the target tissue of the patient to provide electrical stimulation to the target tissue. The one or more electrodes may be coupled directly to the implantable medical device 102 (i.e. without leads) or may be coupled to the implantable medical device 102 via one or more leads.

According to a second embodiment, alternative to the first one, the medical treatment is the action of a medical substance (drug), e.g. insulin. In such second embodiment, the power actuator module 503 may be a pump, controlled by means of the control signal CS, to dispense the medical substance into the target tissue.

In a first embodiment, the substance may be liquid, e.g. insulin.

According to a second embodiment, the substance may be solid, e.g. insulin.

With reference again to the power actuator module 503, according to another embodiment, it can be configured to move a fluid solution from a reservoir into the target tissue of the patient. In particular, in such an embodiment, the target tissue can be an organ of the patient.

The target tissue may include neural tissue (e.g. one or more areas of the brain, the spinal cord, a cranial nerve, or another nerve), a vagus nerve, a trigeminal nerve, a glossopharyngeal nerve, a hypoglossal nerve, muscular tissue (e.g. a heart muscle), or another nerve or tissue.

With reference again to the block diagram of FIG. 5, the implantable medical device 102 further comprises a second communication interface module 504 operatively connected to the RF power receiver module 502. The second communication interface module 504 is configured to communicate data (transmit and receive) with the external RF power transmitter 101 via a wireless link (forward and reverse link), as it will be also explained later. The second communication interface module 504 comprising a coder and a decoder of the communication data, a modulator and other elements configured to performs the functions required to exchange communication data via the forward and the reverse link between the transmitter 101 and the implantable medical device 102. The second communication interface module is configured to operate with a low power wireless communication protocol such as, for example, Bluetooth 4.0, ANT and/or ANT+, Zigbee, and so on.

The implantable medical device 102 further comprises a second programmable control unit 505, e.g. a microprocessor or a microcontroller, operatively connected to the RF power receiver module 502, configured to manage the implantable medical device 102. In fact, the second programmable control unit 505 is operatively connected to all the components of the implantable medical device 102.

The implantable medical device 102 further comprises a reference module 506 operatively connected to both the RF power receiver module 502 and the second programmable control unit 505. The reference module 506 is configured to generate reference current or voltage values used in several functions performed during the operation of the implantable medical device 102, e.g. to generate accurate reference current or voltage values in the case the device delivers current of voltage stimuli.

In particular, the reference module 506 is configured to generate a reference voltage used by a pulse generator module (described later) within the RF power receiver module 502.

In addition, the implantable medical device 102 further comprises an Analog-to-Digital Converter (ADC) module 507 operatively connected to both the RF power receiver module 502 and the second programmable control unit 505. In particular, the ADC module 507 is configured to receive from the target tissue an analog value representative of the target tissue impedance (resistance) and to convert it into a digital value representative of the target tissue impedance, to be sent to the transmitter 101 as a feedback value.

Figure 6:
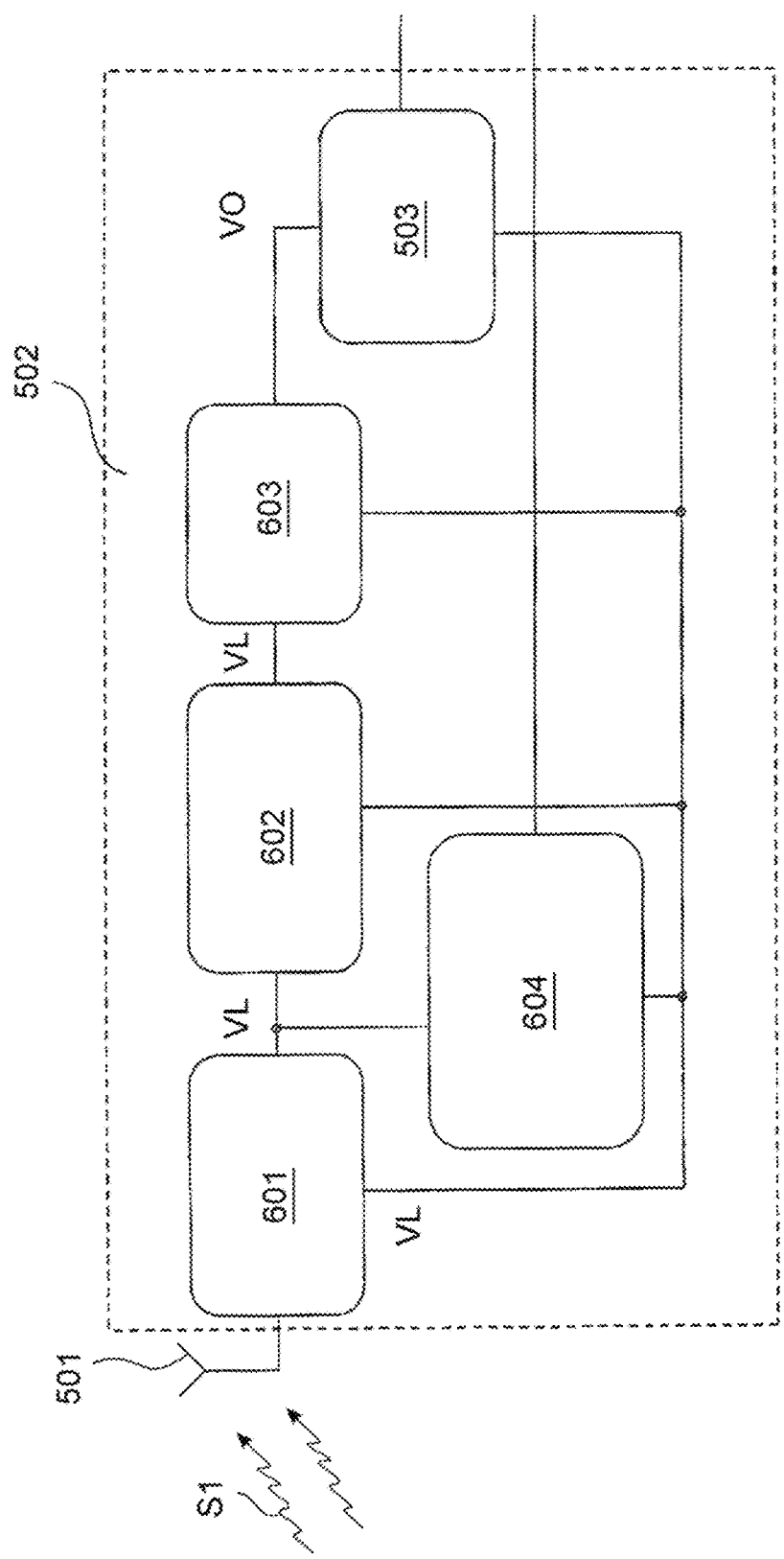
FIG. 6 shows with a block diagram a component of the second portion of the system of FIG. 5.

With reference now to both FIG. 5 and FIG. 6, the RF power receiver module 502 comprises a RF front end module 601 configured to receive from the receiver antenna 501 the first energy signal S1. The RF front end is configured to generate a rectified voltage level VL to be provided to a voltage rectifier, subsequently described, by means of a high Q (Quality) resonant circuit (not shown in the FIG. 6).

The RF power receiver module 102 further comprises an impedance matching network 602 operatively connected to the at least one receiver antenna 501 via the RF front end module 601.

The impedance matching network 602 is configured to match the impedance of the at least one receiver antenna 501 to the other components of the implantable medical device 102 to achieve high efficiency power transfer. For example, the resistance of the antenna may be relatively low, e.g. on the order of a few Ω up to 50Ω, and one or more other components of the implantable medical device 102 may have a comparatively high resistance, e.g. on the order of KΩ. The impedance matching network 601 may facilitate impedance matching from the relatively low resistance of the at least one receiver antenna 501 to a relatively high resistance of some components of the implantable medical device 102.

It should be observed that the radiated power reaching the at least one receiver antenna 501 is limited and depends on the transmitted power, the distance between the external RF power transmitter 101 and the implantable medical device 102, the loss tangent of the target tissue. The efficiency at the maximum power transfer conditions is not higher than 50%. The impedance of the at least one receiver antenna 501 can vary depending on the presence or not of object in the wireless link between the external RF power transmitter module 101 and the implantable medical device 102, the conductivity of the target tissue around the at least one receiver antenna 501 and other parameters. Therefore, the impedance matching network 602 may be preferably of the tunable type.

The RF power receiver module 502 further comprises at least one voltage rectifier 603 operatively connected to the impedance matching network 602. The at least one voltage rectifier 603 is configured to rectify the first energy signal S1 received by the at least one receiver antenna 501 to generate a rectified voltage signal VO, on the basis of the rectified voltage level VL.

The RF power receiver module 502 further comprises the power actuator module 503 (previously described) operatively connected to the voltage rectifier module 603 to receive from it the necessary power to operate.

According to first embodiment, previously introduced, the power actuator module may be a pulse generator configured to provide electrical stimulation on the target tissue via one or more electrodes (not shown in FIG. 6) placed on or in proximity of the target tissue.

According to a second embodiment, previously introduced, the power actuator module may be a pump configured to dispense a medical substance (drug) to the target tissue.

With reference again to the block diagram of FIG. 6, the RF power receiver module 502 further comprises a voltage protection and backscattering module 604 operatively connected to the at least one receiver antenna 501 via the RF front end module 601.

In addition, the voltage protection and backscattering module 604 is operatively connected to all the other modules of the RF power receiver module 502.

Furthermore, the voltage protection and backscattering module 604 is operatively connected to the target tissue (not shown in FIG. 6).

The voltage protection and backscattering module 604 is configured to transmit to the external RF power transmitter 101 feedback information received from the target tissue.

Feedback information comprises patient feedback information, i.e. measured target tissue parameter, typically voltages and conductivity (e.g. impedance), measured patient's vital parameter, e.g. heart rate, and/or medical treatment information, i.e. treatment delivery success/fail information.

It should be observed that the external RF power transmitter module 101 is advantageously configured to control, i.e. stop, pause or restart, the RF power transmission on the basis of said feedback information received from the implantable medical device 102.

In fact, the first programmable control unit 204 of the external RF power transmitter 101 is configured to control, i.e. stop, pause or restart, the RF power transmission, on the basis of said feedback information.

In addition, the external RF power transmitter 101 is configured to detect the feedback information in order to communicate, back to the transmitter 101, tissue impedance values for clinical purposes, in addition to the fact that, in order to make sure that the energy at the RF power receiver module 502 is high enough to actuate the neural stimulation, a feedback of successful operation to the transmitter is generally desirable.

Furthermore, in the case exceeding energy is transferred to the RF power receiver module 502, rather than wasting energy by partially cloaking the RF power receiver module 502, the level of transmitted power could be lowered in order to save battery energy.

If the external RF power transmitter 101 is configured to detect the shunting of the at least one receiver antenna 504, the transmitted power could be reduced, otherwise the operation of the receiver output voltage protection could be transmitted back to the transmitter by backscattering modulation.

Figure 7:
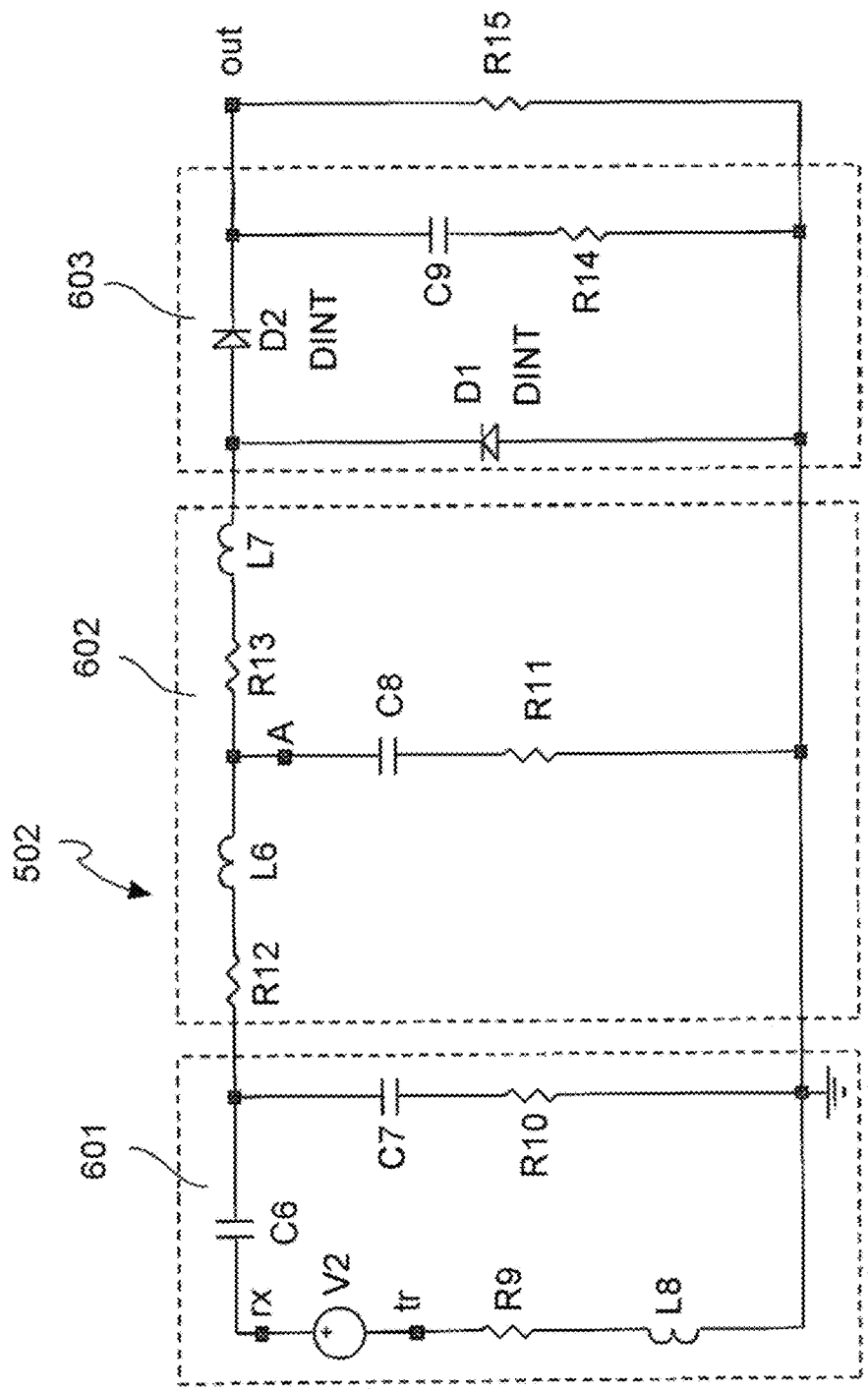
FIG. 7 shows with an electric circuit the second portion of FIG. 5 according to an embodiment of the present disclosure.

With reference to FIG. 7, the implantable medical device 102 is represented by a circuital point of view in accordance with an embodiment of the present disclosure.

A first resistor R9 and a first inductance L8 represent the antenna impedance at the frequency of 433.92 MHz.

A first capacitor C6, a second capacitor C7, a second inductance L6, a third capacitor C8 and a third inductance L7 represent the tunable impedance matching network 602. All the resistors in this impedance matching network are parasitic components. By making the second capacitor C7 and the third capacitor C8 as variable capacitors, the impedance matching network can be tuned to match the load to the antenna impedance for various values of antenna impedance. This is possible assuming to have enough power stored or received to enable the tuning of the capacitors. If the RF power receiver module 502 is totally detuned, no power may be received to enable the tuning of the impedance matching network resulting in failure. Therefore, it is very important to set the default values of the tuning capacitors such a reasonable amount of energy is transferred to start up the circuit of the RF power receiver module 502.

With reference again to the electric circuit of FIG. 7, a first diode D1 and a second diode D2 represent the voltage rectifier 603 configured to transform the first energy signal S1 (AC RF signal) into a DC reference voltage VO. The forward voltage and the parasitic capacitance of the first diode D1 and the second diode D2 guarantee high efficiency for the circuit.

A fourth capacitor C9 is the output filter capacitor and represents the element able to charge/discharge the energy needed to power the power actuator module.

A second resistor R15 represents the continuous load, i.e. the power actuator module.

Figure 8:
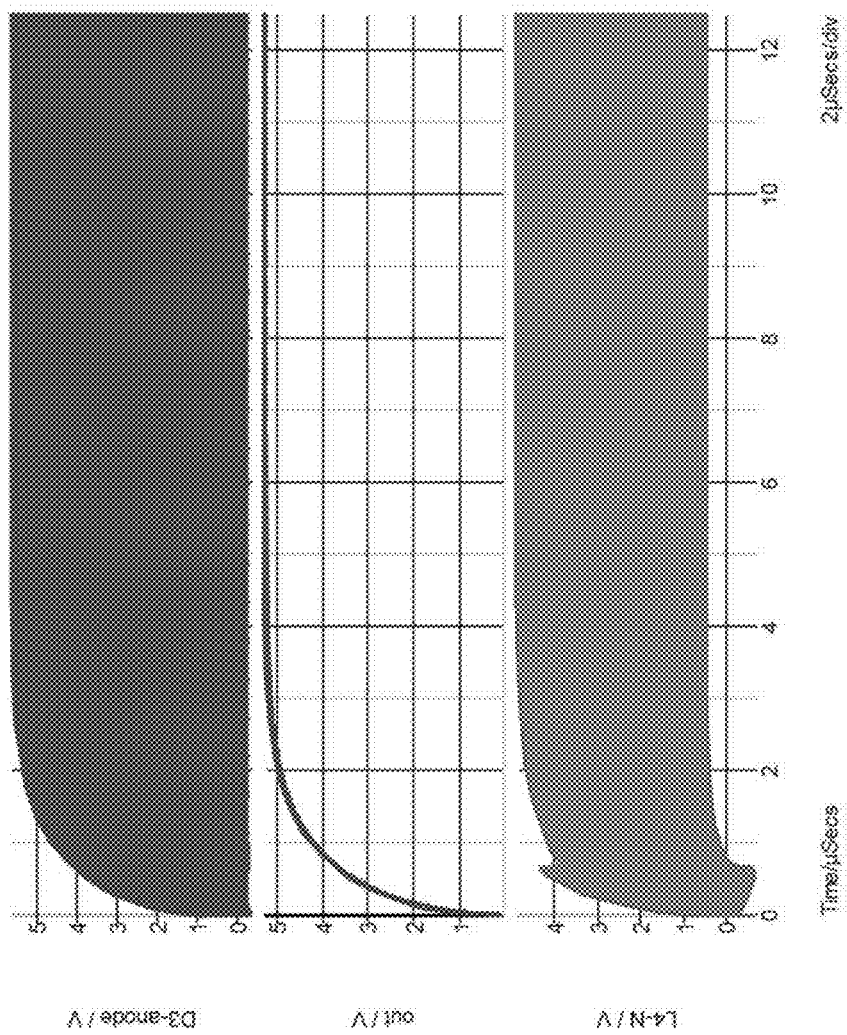
FIGS. 8, 9, 10 and 11 illustrates with diagrams waveforms obtained with simulations performed on the electric circuit of FIG. 7.

With reference to FIG. 8, main simulated waveforms of the RF power receiver module 502 as represented by the electric circuit of FIG. 7 are represented, in the case the output filter capacitor C9 has a value of 100 pF.

In particular, the first (upper) waveform is the voltage of the anode of the second diode D2, the second (in the center) waveform is the output voltage (node OUT) and the third (lower) waveform is the voltage at the node named as A.

Figure 9:
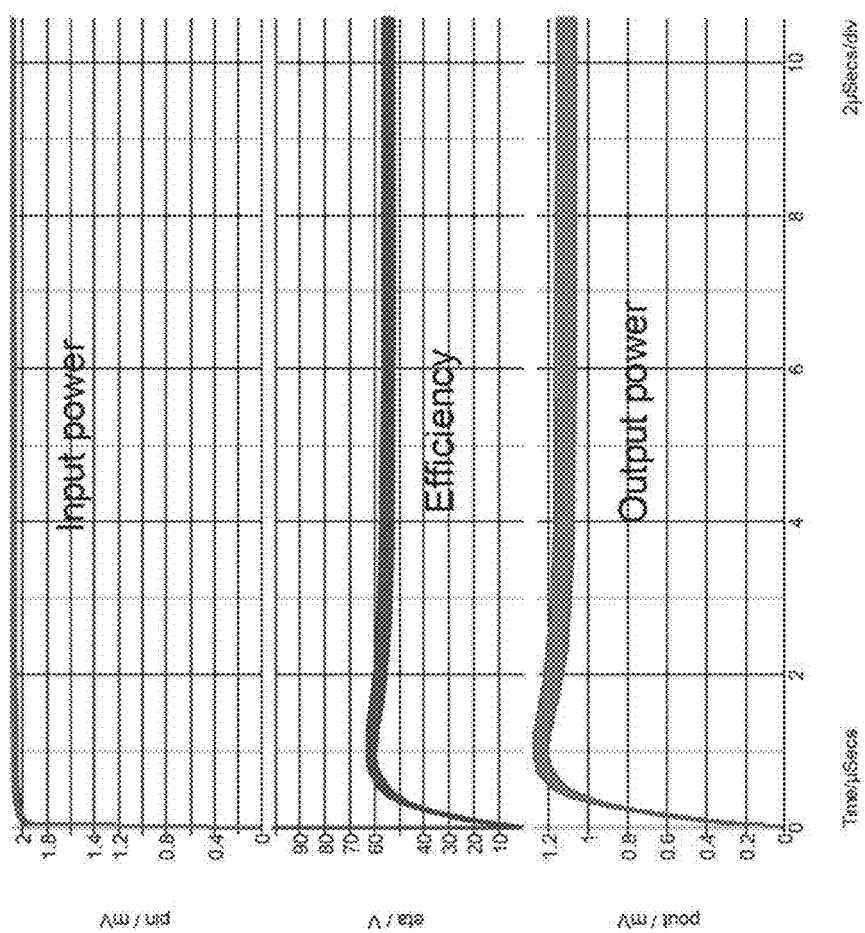

With reference to FIG. 9, dynamic powers for the same simulation are represented.

In particular, the input power (upper waveform) is limited to about 2 mW (power units are indicated in mV but they should be indicated in mW) and the output power (lower waveform) is in excess of 1 mW.

It can be also noted that the efficiency (center waveforms), also indicated as V in the diagram but computed directly as percentage) after the initial peak around 60%, is settled at values slightly in excess of 50%.

The antenna impedance may vary depending on the operating conditions.

Figure 10:
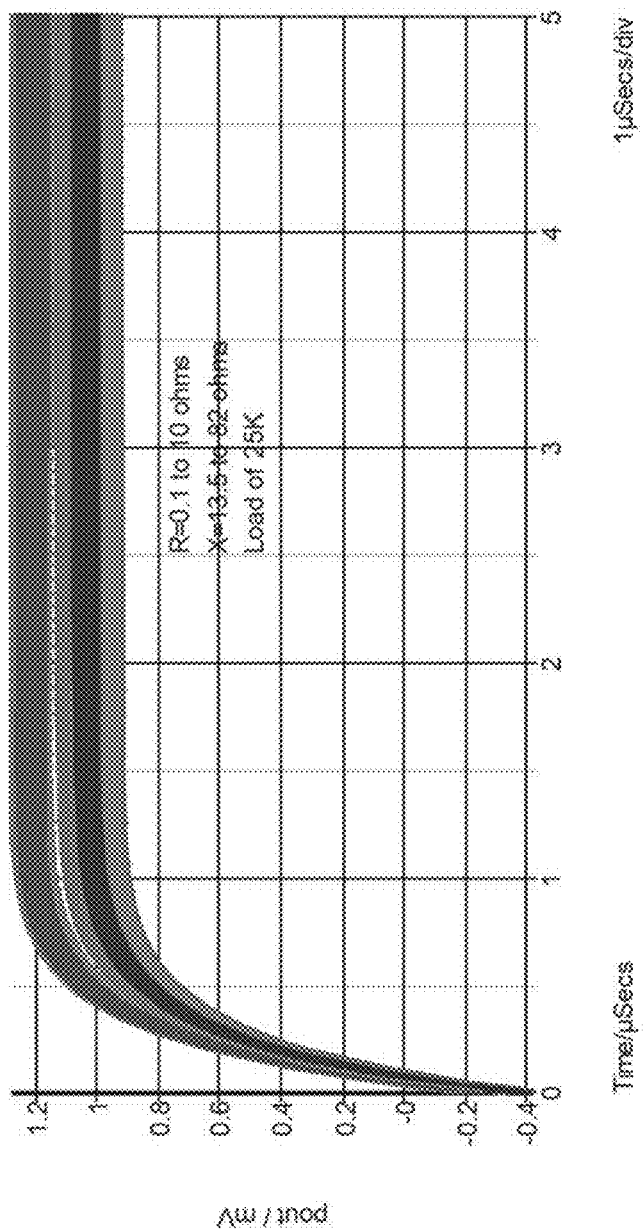

In particular, with reference to FIG. 10, it has been verified that for values of the first resistor R9 (real part) between 0.1Ω and 10Ω with the imaginary part between 13.5Ω and 82Ω, the impedance matching network 602 can be tuned to guarantee an efficiency in the order of 50% with a load (second resistor R15) of 25 KΩ.

With reference to FIG. 8, the implantable medical device 102 is presented by a circuital point of view in accordance with a further embodiment of the present disclosure.

It should be observed that when the reactive part of the antenna impedance changes, rather than tuning the first capacitor C6 to maintain the resonance, it is preferable to tune the second capacitor C7 to re-adjust the impedance and bring back the desired efficiency.

However, the first capacitor C6 is important to guarantee high enough voltage level at the output by de-coupling the antenna impedance from the rest of the electric circuit of FIG. 7.

Furthermore, the first capacitor C6 could be considered part of the at least one receiver antenna 501 if its impedance becomes capacitive (negative reactance) and it will allow the desired performance for the receiver also in that case.

The impedance that the electric circuit sees looking into the voltage rectifier 603 is quite high both in its real part and in its imaginary part. The real part can be estimated to be close to 100Ω and its imaginary is positive and can be estimated to be around 400Ω. The impedance matching network 602 of the RF power receiver module 502 is very flexible.

Turning back to the load, as mentioned above, the load is typically the output filter capacitor C9 (fourth capacitor C9) until it gets charged to the desired voltage (e.g. 5V) for neural pulse discharge during neural stimulation, in the case the power actuator module is directed to perform electronic stimulation.

Therefore, it has been verified that the efficiency remains high for much of the charging time without any specific resistive load.

Figure 11:
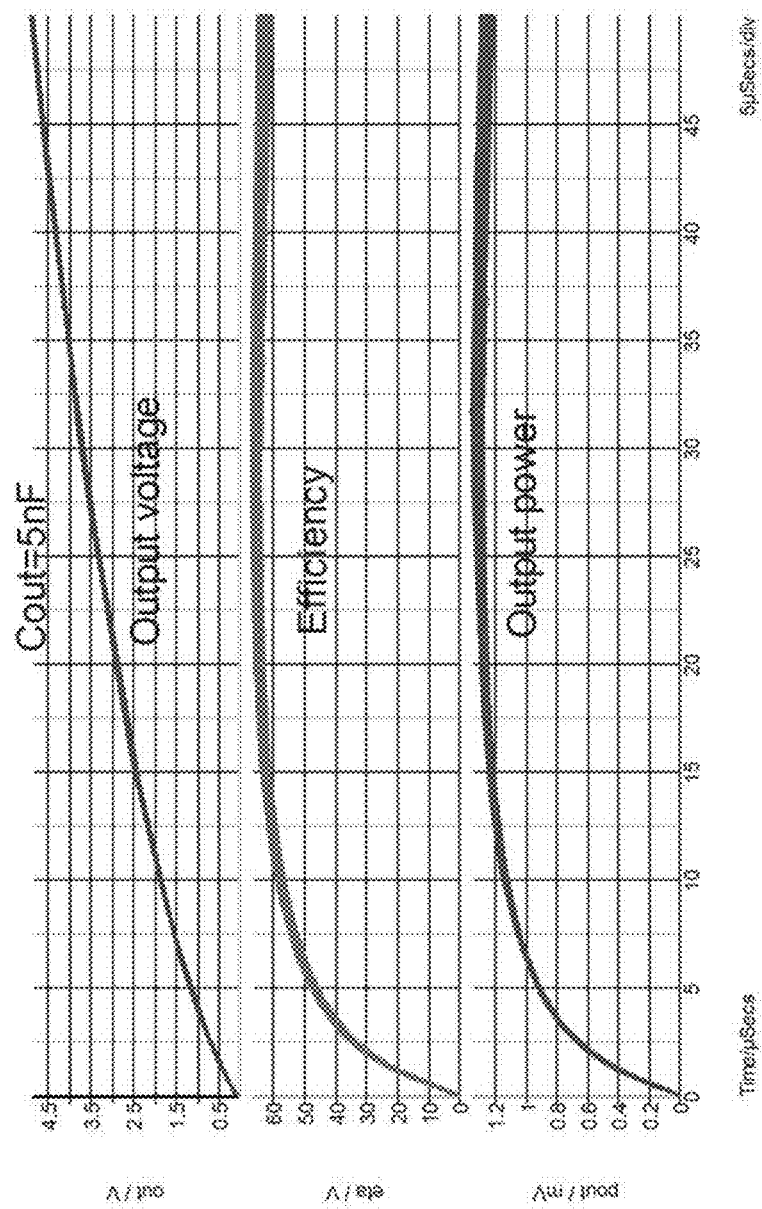

With reference now to FIG. 11, simulated waveforms are shown corresponding to the electric circuit of FIG. 7 but without the load resistor of 25 KΩ and with the output filter capacitor C9 of 5 nF.

It can be noticed that during the charge of the output filter capacitor C9, between 1 V and 5 V of values of the output voltage, the efficiency remains high (with peaks in excess of 60%) which is desirable. Initially, there is a dip of the output power, but that is not corresponding to reality because it is due to the low pass filtering of the output power. The simulation illustrated in FIG. 11 has been performed with a real part of the antenna impedance of 1Ω. It is clear that if the resistive part of the at least one receiver antenna 501 is higher the efficiency values are lower for lower output voltages, and thus the time it takes to charge the output filter capacitor is longer. It has been verified that for antenna equivalent resistance of 70Ω the time would be about twice as long. The RF power receiver module 502 is anyway sized so that the efficiency is higher for values of output voltage around 4-5 V.

Returning back to the RF power receiver module 502, it should be observed that one of its important aspects is the ability to operate without injecting harmonics in the antenna current. The presence of the voltage rectifier, being a non-linear circuit, inherently introduces harmonics with significant amplitude in the current. These harmonics are very undesirable because they get transmitted back from the at least one receiver antenna 501 and could be disturbing other circuits and RF communication links. In particular, the most difficult harmonic frequency to suppress is the third one (having a frequency of 1.3 GHz).

By forcing the output voltage to be around 5 V, the impedance of electric circuit of FIG. 7 does not change with the output voltage and the electric circuit can be simulated with an input power of 2 mW (without power limiting voltage source, but with simplified behavioral mutually coupled transmitter circuit) to analyze the spectrum of the antenna current.

In particular, it has been observed that the third harmonic frequency is quite high (about 45 dB below the carrier frequency).

Therefore, it needs to be filtered of anyway attenuated at least 60 dB below the fundamental harmonic frequency.

Figure 12:
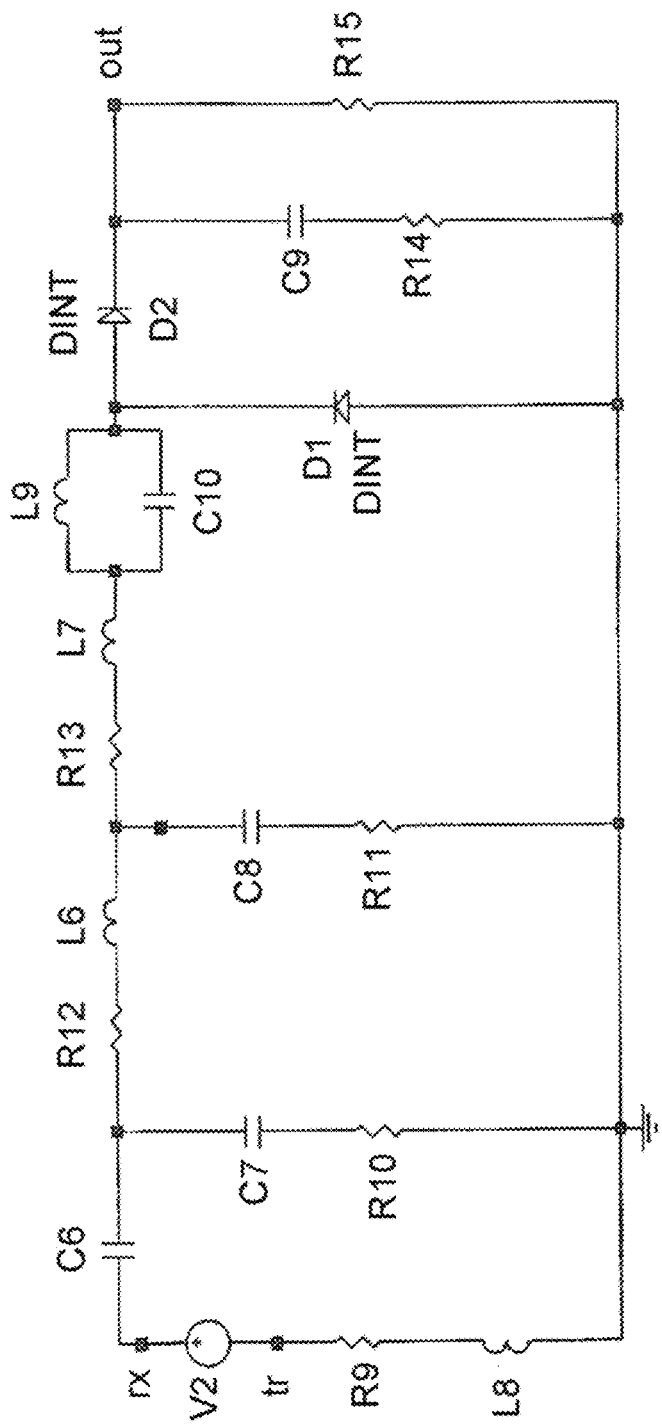
FIG. 12 shows with an electric circuit the first portion of FIG. 5 according to a further embodiment of the present disclosure.

In order to obtain that, with reference to the electric circuit of FIG. 12, a first order resonant filter L9, C10 has been placed on the left of the second diode D2. The first order resonant filter L9, R10 is resonant at the third harmonic frequency and the impedance of the parallel circuit is very high at that frequency. The first order resonant filter L9, C10 introduces a minor attenuation but it is within acceptable levels.

Figure 13:
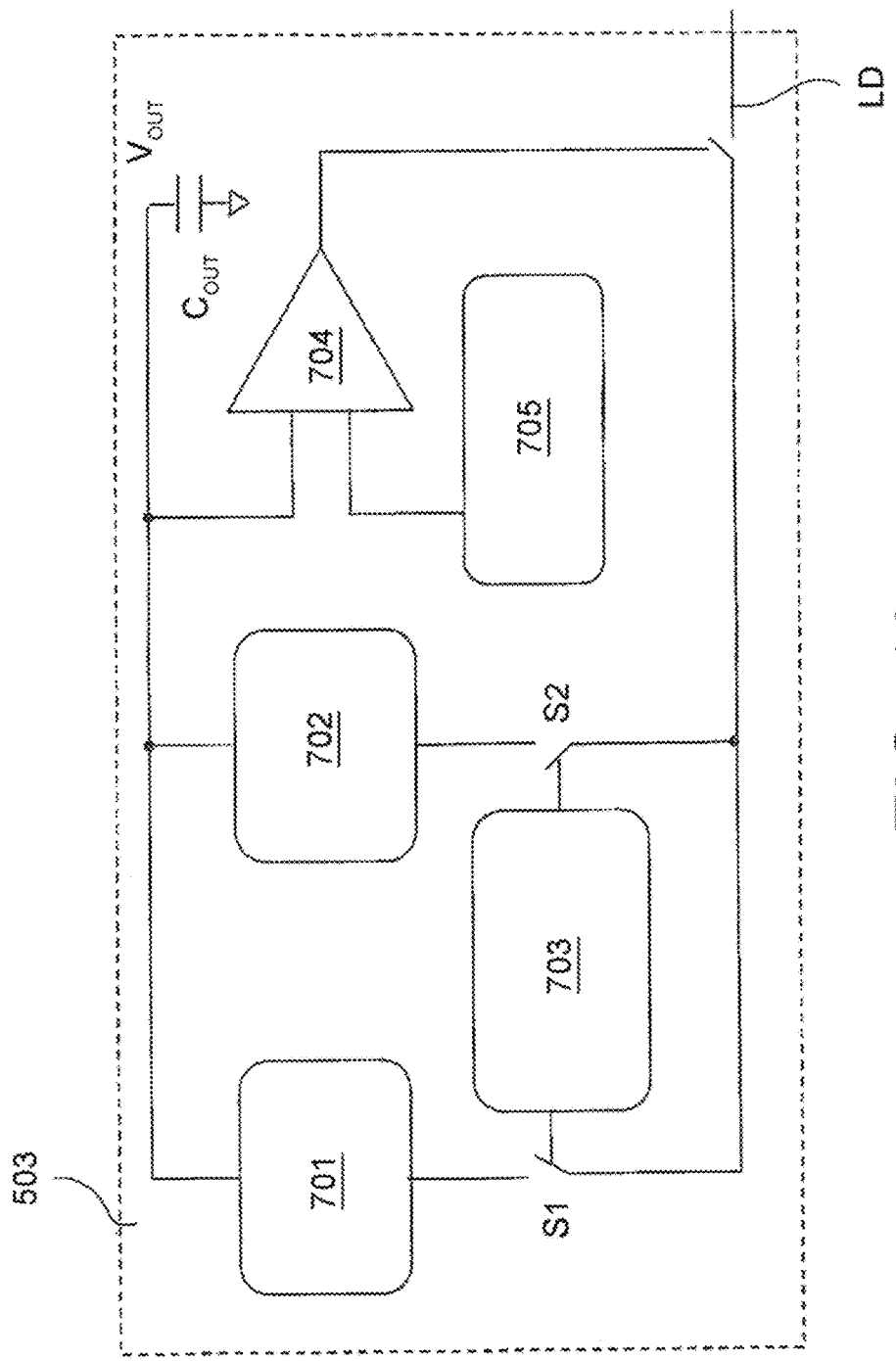
FIG. 13 illustrates a block diagram of a further component of the second portion of the system of FIG. 5.

With reference now to FIG. 13, a power actuator module 503, according to the embodiment wherein it is configured to perform electronic stimulation of the target tissue, is now described. In other words, in FIG. 3, the power actuator module 503 is an electronic pulse generator, i.e. a neural pulse generator.

The power actuator module 53 comprises a current regulator 701 from the output voltage Vout to a lead LD to the one or more electrodes (not shown in the FIG. 13). The current regulator 701 is connected to the lead LD via a first switch S1. The current regulator 701 may be a current mirror.

In addition, the power actuator module 503 further comprises a voltage regulator 702 from the output voltage Vout to the lead LD to the one or more electrodes. The voltage regulator 702 is connected to the lead LD via a second switch S2.

The voltage regulator 701 can be implemented with a LDO (Low Drop-Out) regulator. In alternative, a buck switching power converter could be used. As a third alternative, if the output capacitor Cout filtering the output voltage Vout is large enough to not drop its voltage significantly during the electronic stimulation (e.g. neural stimulation), the output voltage could be directly regulated to be at a preset therapy voltage (e.g. 3.6 V) rather than 5 V.

The power actuator module 503 further comprises a Voltage and Current Mode Selection module 703 configured to control both the first switch S1 and the second switch S2.

In particular, the Voltage and Current Mode Selection module 703 is configured to select the electronic stimulation mode by opening/closing the first switch S1 and closing/opening the second switch S2, respectively.

According to the embodiment of FIG. 13, the power actuator module 503 further comprises a comparator module 704, i.e. an operational amplifier, configured to compare the output voltage Vout with a programmable voltage reference 705. The output of the comparator module 705 is operatively connected to the lead LD to the one or more electrodes via a third switch S3. In particular, the comparator module 704 is configured to control the third switch Se (opening/closing) on the basis of the result of the comparison of the output voltage Vout and the programmable reference voltage output 705.

It should be observed that the programmable reference voltage output 705 should be set such that knowing the value of the output capacitor Cout and its regulated voltage, the timing of the pulse could be determined by computing the voltage drop on the output capacitor Cout during the pulse. The comparator module 704 is configured to open (turn off) the third switch S3 when the programmable reference output voltage (threshold) has been reached.

Alternatively, an analog or digital timer should be designed to determine the duration of the pulse.

According to an alternative embodiment, the output of the comparator module 705 could be directly connected to the Voltage and Current Mode Selection module 703 in order to directly control the opening/closing of the first switch S1 and the second switch S2.

Figure 18:
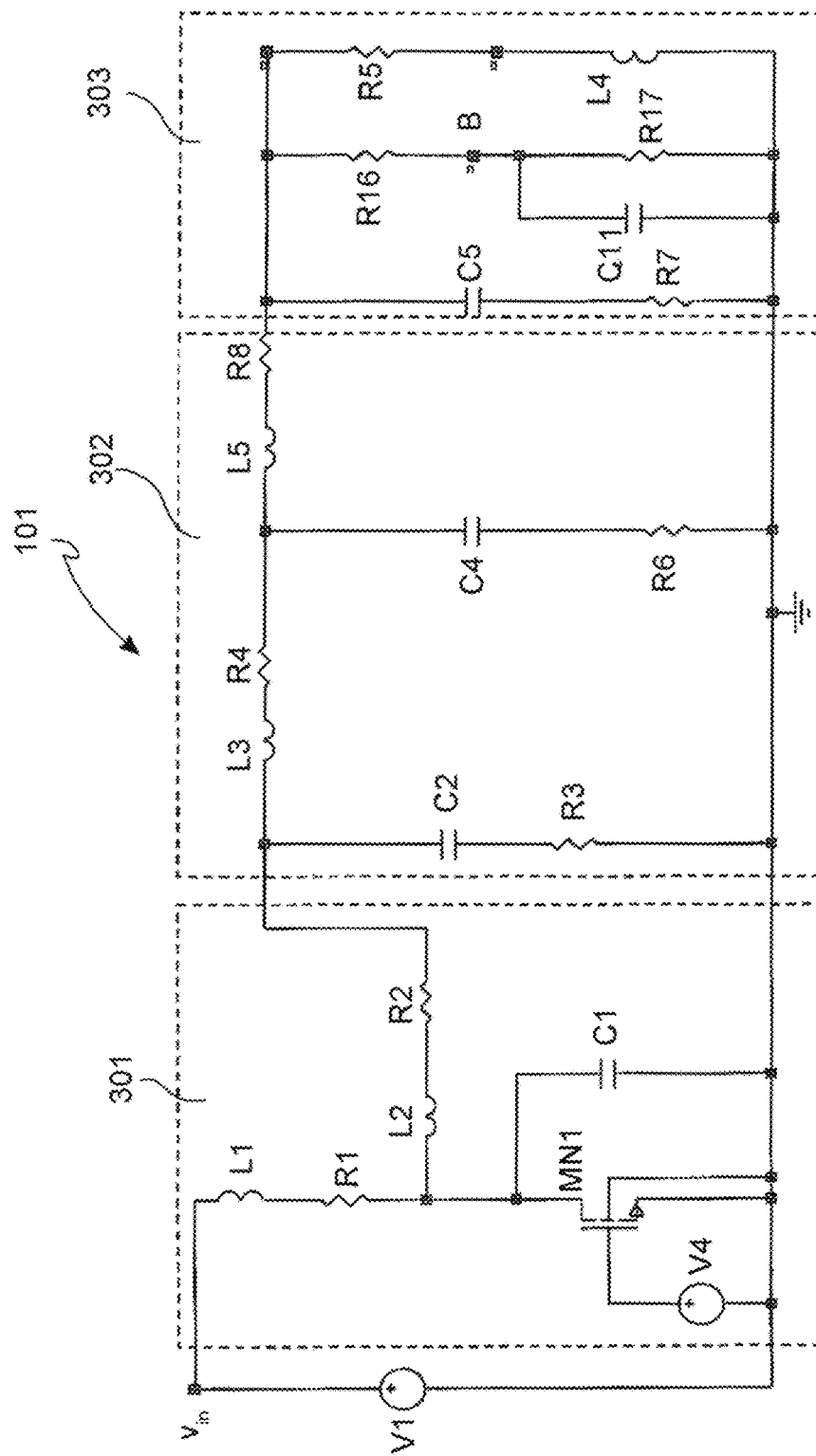
FIG. 18 illustrates an electric circuit of the first portion of the system of FIG. 2, according to a further embodiment of the present disclosure.

With reference now to the electric circuit of FIG. 18, the external RF power transmitter 101 of the system 100 is represented by a circuital point of view in accordance with another embodiment of the present disclosure.

With reference to the previous embodiment illustrated in FIG. 4, the transmitter 101 of FIG. 18 comprises a further filter represented by the resistors R16 and R17 with the capacitor C11. A backscattering filtered signal (feedback information, as previously described) is detected at the node B of the circuit.

As an example, the reverse link communication can be implement as ASK modulation between two levels of amplitude. The modulation depth should be quite high in order to guarantee reception of the signal and this prevents the charge of the receiver capacitor (effective transfer of energy) during reverse link communication.

Figure 19:
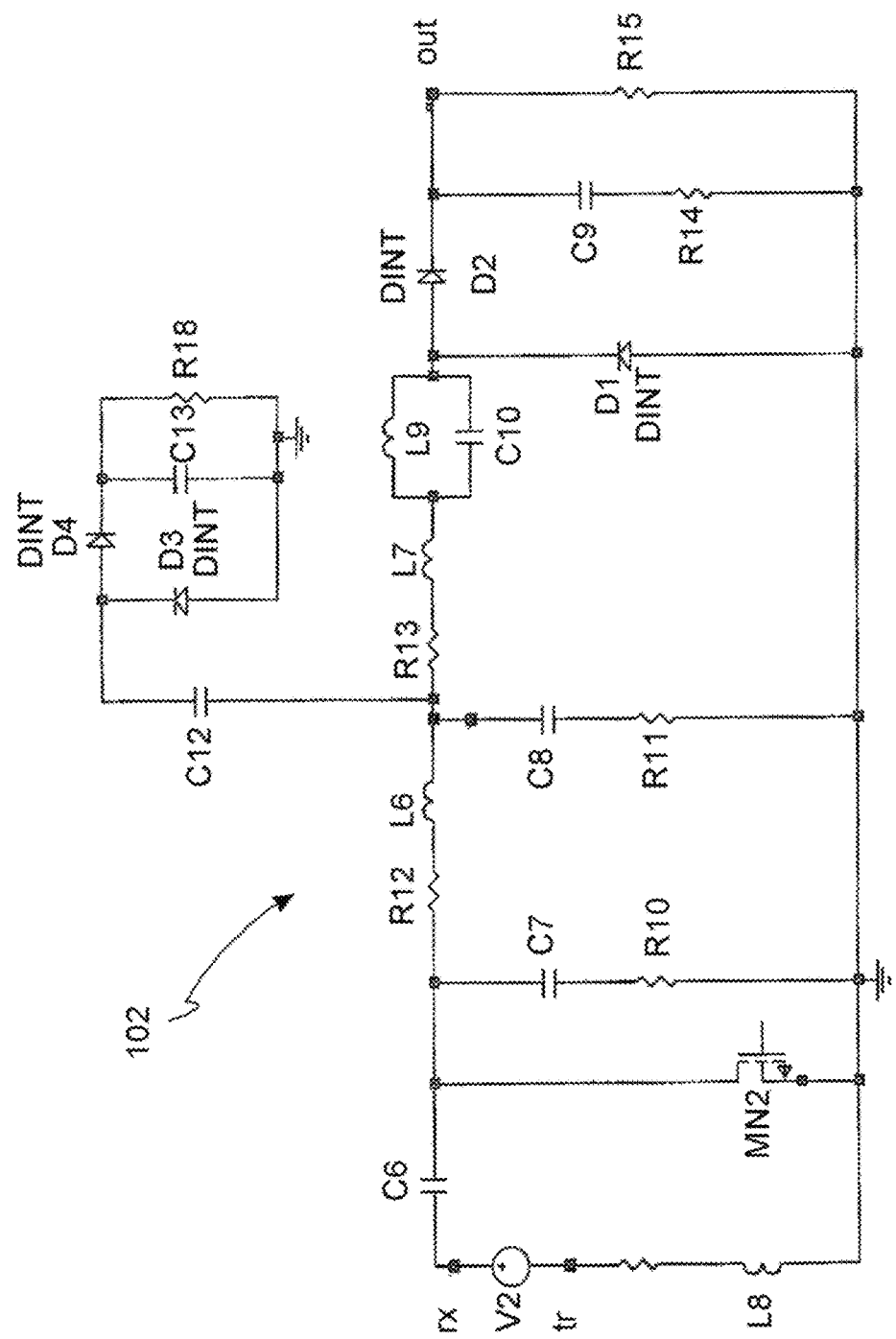
FIG. 19 illustrates an electric circuit of the second portion of the system of FIG. 5, according to a further embodiment of the present disclosure.

With reference now to the electric circuit of FIG. 19, the implantable medical device 102 is represented by a circuital point of view in accordance with another embodiment of the present disclosure.

The RF power receiver module 502 comprises a ASK demodulator typically implemented as an AC coupled envelope detector coupled to the output of the impedance matching network.

The ASK modulation detector is basically an envelope detector AC coupled to the node A of the RF receiver power module. It is very important that this circuit does not attenuate significantly the main signal in order not to degrade the efficiency of the system 100. The power consumed by the ASK demodulator and other coupled blocks has to be minimum and negligible with respect to the desired output power.

The transistor MN2 is used for the backscattering modulation for reverse link communication. The transistor MN2, when turned on and off at a given frequency, shunts the antenna thus altering its impedance and this variation is reflected back to the transmitter 101.

Figure 20:
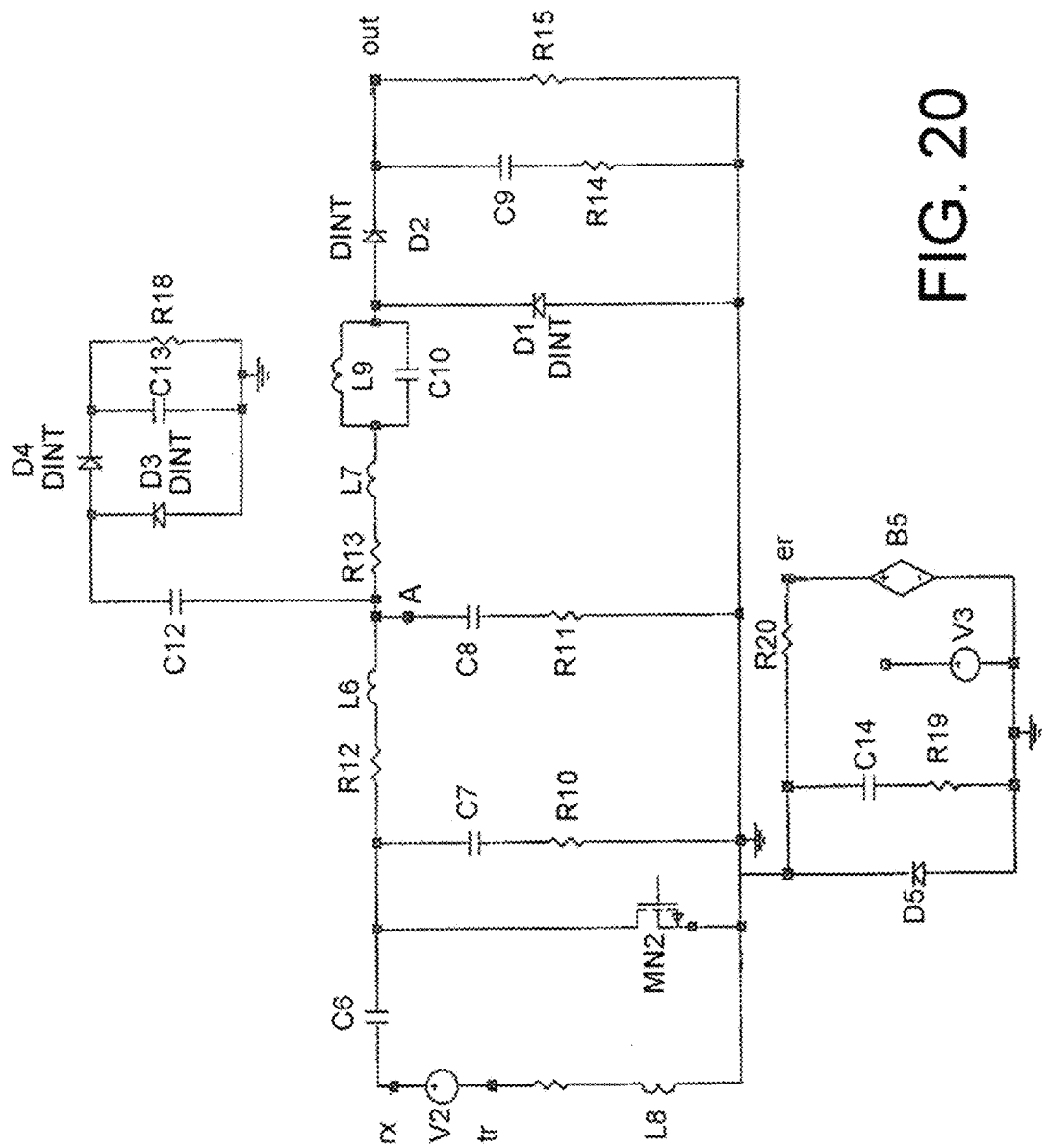
FIG. 20 illustrates an electric circuit of the second portion of the system of FIG. 5, according to a further embodiment of the present disclosure.

With reference now to the electric circuit of FIG. 20, the implantable medical device 102 is represented by a circuital point of view in accordance with another embodiment of the present disclosure.

Although the RF power receiver module 502 can be designed to have the highest efficiency when its output voltage is between 4 V and 5 V, when the RF receiver power module 502 has no continuous load (only the output capacitor C9 as a load), the output power does not drop for voltages higher than 5V, because the open load output voltage is much higher than 5V.

However, the output voltage could and should be limited, and therefore the components of the RF power receiver module 502 needs to be protected from over-voltages by the use of a linear regulation circuit. In fact, a linear regulation guarantees constant output voltage without introducing undesired harmonics at the at least one subcutaneous receiver antenna.

As illustrated in FIG. 20, a simple Operational Transconductance Amplifier (OTA), a voltage reference with an output filter configured to drive the transistor MN2 shunting the antenna can regulate the output voltage out at the desired voltage.

Of course, given the small power values, it would be simpler and inexpensive to use a Zener diode at the output for protection purposes, but the shunt transistor is the same one that can be used for backscattering modulation as well, as long as it is driven fully on or fully off when communicating in reverse link. The proposed circuit is more accurate and even though a Zener diode would consume no current until it is forward biased, the proposed circuit can be made very efficient.

The controlled voltage source B5 represents a behavioral comparator to compare the reference (ideal voltage source V3) with the output voltage, the further resistor R20 represents the transconductor and the further capacitor C14 along with the series resistor R19 defines the pole-zero filter of the OTA. The further diode D5 is a simple clamp to prevent large negative voltages at the gate terminal of the transistor MN2.

It should be noted that the entire system 100 has been simulated to better emulate the final system and in particular to understand the interactions between the external RF power transmitter module 101 (transmitter) and the implantable medical device 102 (receiver).

In order to simulate the system 100, it has been decided to utilize mutually coupled inductances to analyze the interaction between the transmitter and receiver module. Typically, this is more appropriate for inductive coupling and/or near field wireless power transfer types, however the main phenomena are quite similar provided that the proper coupling coefficient between the two coupled inductances is used. The coupled inductances are the inductive part of the antennas, provided that their impedance at the selected frequency has an inductive component.

Figure 21:
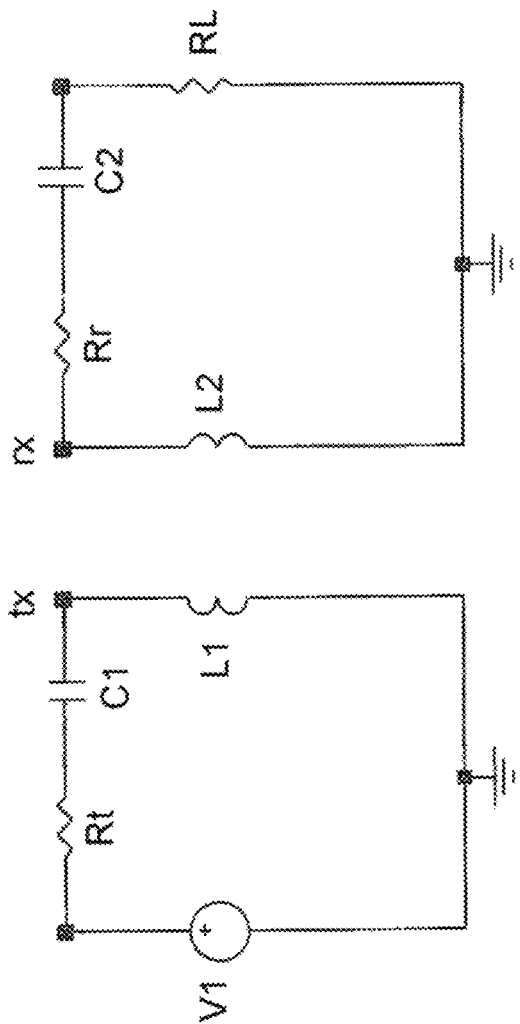
FIG. 21 illustrates with an electric circuit a representation of the system of the present disclosure.

The coupling coefficient can be determined using the electric circuit represented in FIG. 21.

In this specific case the two coupled inductances are equal in value, but since the antenna impedance varies, the change in the coupling coefficient, if one or both inductances change, has to be taken into account.

By developing the equations for the electric circuit of FIG. 21, it can be obtained:

$$\eta = \frac{P_{load}}{P_{V1}} = \frac{\omega^2 M^2 R_L}{(R_r + R_L)[R_t(R_r + R_L) + \omega^2 M^2]}$$

therefore, the efficiency, from the source, at the transmitter side, all the way to the load, is defined as a function of the resistors, of the frequency and of M (mutual inductance). $M=k\sqrt{L_1L_2}$ (or $M=kL$ if $L1=L2$) where L is the resonant inductance and K is the coupling coefficient.

If Rr<<RL the equation above is simplified to:

$$\eta = \frac{P_{load}}{P_{V1}} = \frac{\omega^2 M^2}{(R_t R_L + \omega^2 M^2)}$$

For the particular case in which $L1=L2=L$, and assuming that $\eta<<1$ (in our case it is in the order of 0.001) the equation above leads to:

$$k = \frac{\sqrt{\eta R_L R_t}}{\omega L}$$

So, by knowing the equivalent real part of the impedance both for the transmitter circuit and for the receiver circuit, and the ratio between the power received and the power transmitted by the antennas (which in this case it is dependent on the distance between the transmitter and the receiver, on the antenna gains and on the conductivity of the tissue around the receiver antenna), the value of K to simulate the system could be determined.

In reality it is quite difficult to estimate the Rt and RL both for the transmitter and for the receiver because both circuits are not linear (the first one is not linear because there is a switch and the second one because there is a diode rectifier).

In addition, since the impedance of the transmitter varies with the output voltage, the effect is that for the same k, the power received by the receiver changes as well with the output voltage.

However typically it can be assumed that the output voltage remains at about 5V during all the neural stimulation session. Therefore, the system has been designed to have the highest efficiency around the output voltage range from 4V to 5V.

With reference now to the diagram of FIGS. 22-25, simulations of the system 100 will be now briefly described.

A large number of simulations have been performed with a large output capacitor set a given voltage.

Figure 22:
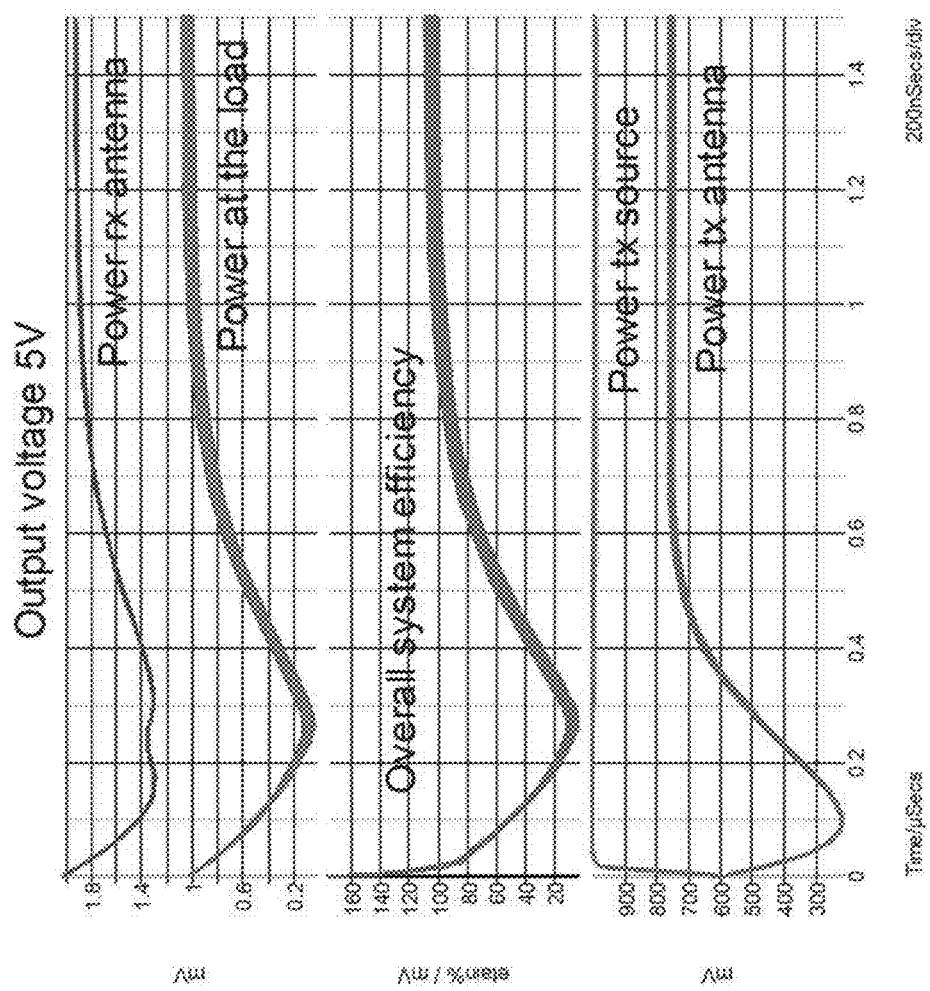
FIGS. 22, 23, 24 and 25 illustrate with diagrams waveforms obtained with simulations performed on the system of the present disclosure.

A first simulation has been performed with an output voltage of 5 V. The diagram of FIG. 22 shows the various dynamic power levels involved.

It can be noticed that the power used, after the initial transient due to the settling of internal node voltages, by the source of the transmitter is about 1W, the one obtained at the transmitter antenna is in excess of 700 mW, the power received at the receiver antenna is almost 2 mW (this assumes a path loss of 25.7 dB) and the power received by the load is about 1 mW.

The middle waveform of FIG. 12 represents, in dynamic form, the overall efficiency of the system 100 in percentage which is supposed to be at least of 0.1% (1/1000). All this was done with a coupling coefficient of about 0.088 because the effective resistance of the transmitter and of the receiver circuit in their final form is quite high. For instance, it has been computed that for the receiver with no resistive load it is in the order of 144Ω. This factor increases the coupling coefficient for the same overall efficiency.

Figure 23:
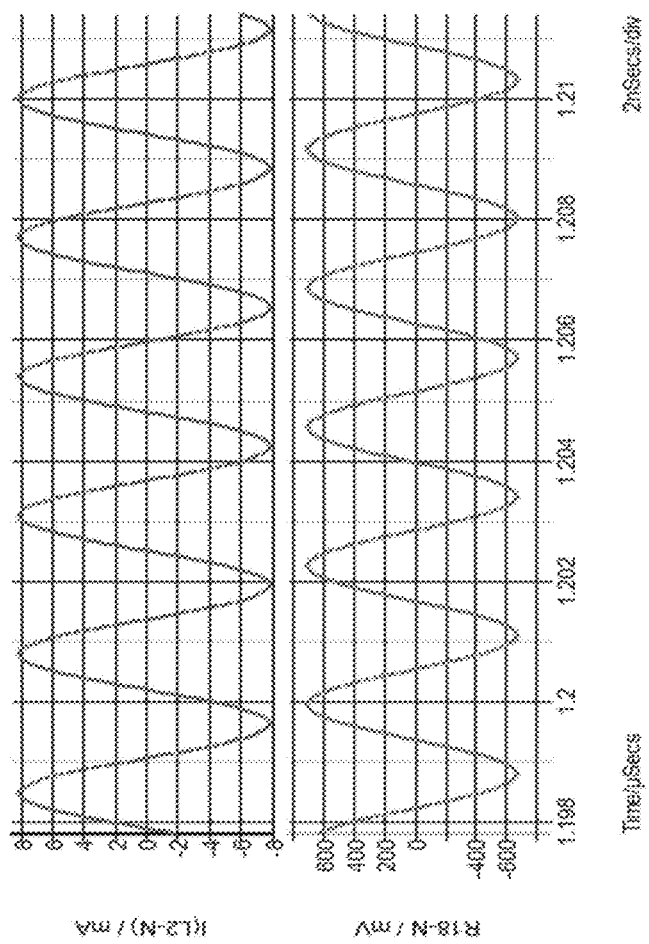
Figure 24:
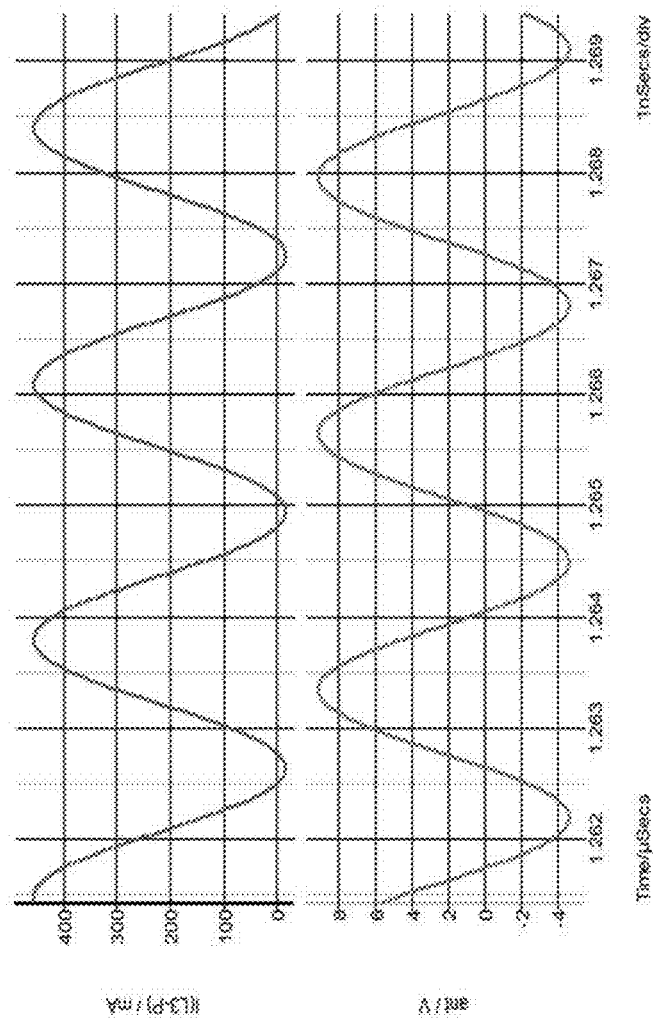

In the specific case described above the obtained voltage and current waveforms at the receiver antenna are shown in the diagram of FIG. 23 and the current and voltage waveforms obtained at the transmitter antenna are illustrated in the diagram of FIG. 24.

It should be noted that this case is for a specific antenna impedance. The voltages and currents vary for different antenna impedances.

In addition, it is also important to verify and guarantee that the system 100 is able to charge the output capacitor C9 starting from an initial condition of being totally discharged.

Figure 25:
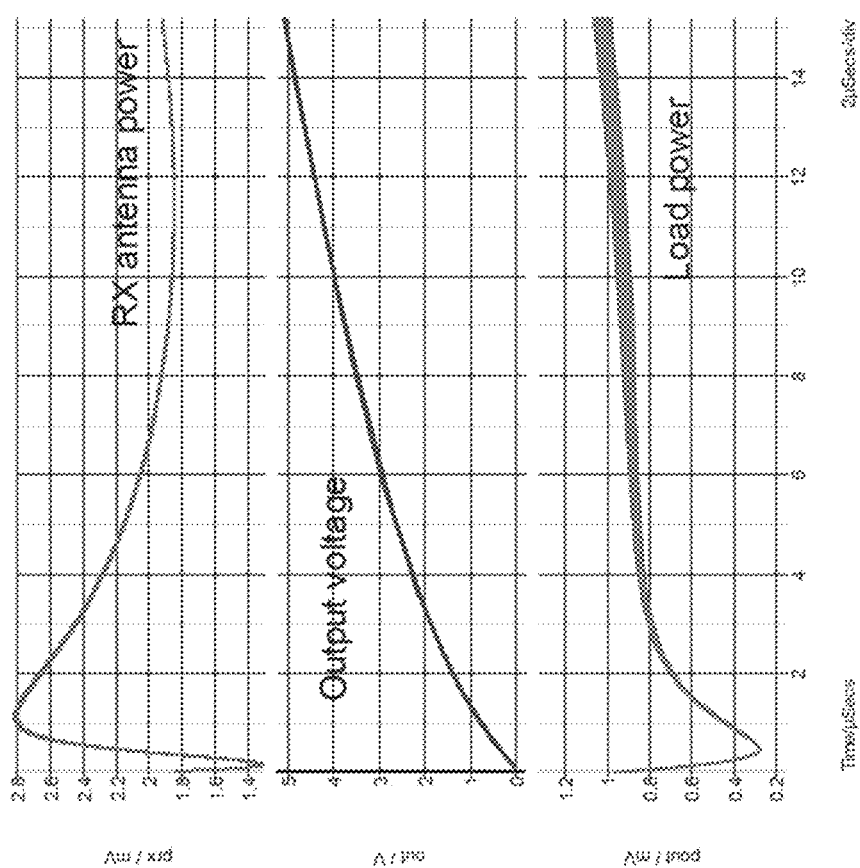

The diagram of FIG. 25 shows a simulation of that condition where the output capacitor value was reduced to 1 nF to prevent very long simulation times.

It should be observed that for output voltages below 2V, although the power received at the receiver antenna is in the order of 2 mW or more, the efficiency of the RF power receiver module is quite low. This is because, as explained earlier, the efficiency of the RF power receiver module changes with its output voltage and it has been designed such that its efficiency is maximum at higher voltages (higher than 4V).

In this case the charge time was about 14 μs, which would imply that for a 1 μF output capacitor it would take something in the order of 15 ms, but again for different antenna impedances the charging times would vary as well. The simulations illustrated in FIG. 25 were performed with 10Ω of antenna resistance for the transmitter side and 5Ω of antenna resistance for the receiver side. These values are quite conservative and it is evident that if the resistance values were smaller the charging times would be shorter.

One of the initial objective of the present study was the ability to operate the neural stimulation device without the need for an implanted battery, but one of the possible future variants of the system is the use of a super capacitor in place of the battery so as to allow the therapy for a longer periods of time without the need to transmit always the RF power. The performed simulations showed that such system will be supported by the designed receiver without major modifications to the circuit.

It should be also mentioned that during the system simulations it was observed that the impedance seen by the power amplifier of the transmitter was slightly different from what simulated with the transmitter only. In fact the overall efficiency was slightly lower due to the fact that the ZVS conditions were not perfectly met any more. This observation has led to the need to increase the capacitor C1 of FIG. 18 from 40 pF to 50 pF.

The electronic medical system according to the embodiments of the present disclosure, allows to overcome the disadvantages described above with reference to the prior art.

This is due mainly to the fact that the implantable medical device of the system of the present disclosure does not need the presence of an implanted battery as the system and/or the device of the prior art.

In fact, avoiding the presence of a battery, there are no problems related to its presence, i.e. the need of its replacement by surgery, the impossibility of performing Magnetic Resonant Imaging (MRI) test, the presence of heavy metals and other potentially hazardous material, such as mercury, cadmium, nickel, and lithium, requiring extra care for disposal avoiding leakage.

In addition, as expected, the overall efficiency of the system is quite low (0.1%) and that is due to the nature of the far field RF power transmission, however the system appears to be able to meet the initial requirements of enabling the operation of a simple neural stimulation device implanted subcutaneously without the need for an implanted battery for distance between the transmitter antenna and the receiver antenna in the 10 to 40 cm range at the frequency of 433.92 MHz.

A man skilled in the art may make several changes, adjustments and replacements of elements with other functionality equivalent ones to the embodiments of the electronic medical system described above in order to meet incidental needs, without departing from the scope of the following claims. Each of the features described as belonging to a possible embodiment can be obtained independently of the other embodiments described.

The invention claimed is:

1. An electronic medical system, comprising:
an external RF power transmitter configured to emit a first energy signal via an electromagnetic coupling, said external RF power transmitter being configured to emit said first energy signal with a power no greater than 1 W;
an implantable medical device comprising:
at least one receiver antenna configured to receive said first energy signal via the electromagnetic coupling;
an RF power receiver module operatively connected to the at least one receiver antenna, the RF power receiver module being configured to extract a second energy signal having a power of at least 1 milliwatt (mW), the RF power receiver module being powered by said second energy signal, the RF power receiver module being configured to generate a control signal;
a power actuator module, operatively connected to the RF power receiver module, powered by said second energy signal, the power actuator module being configured to receive said control signal, the power actuator module being configured to deliver a medical treatment to at least a target tissue of a patient on a basis of said control signal; and
wherein the implantable medical device comprises a RF front end module, an impedance matching network, a voltage rectifier, the power actuator module, and a voltage protection and backscattering module; and
wherein the implantable medical device further comprises a second communication interface module operatively connected to the RF power receiver module, said second communication interface module being configured to communicate data with the external RF power transmitter via a wireless link.

2. The electronic medical system of claim 1, wherein the medical treatment is an electronic stimulation, the power actuator module comprising a pulse signal generator configured to apply electrical stimulation to the target tissue, controlled by means of the control signal, providing electrical stimulus to one or more electrodes connected to the target tissue.

3. The electronic medical system of claim 1, wherein the medical treatment is an action of a medical substance, the power actuator module comprising a pump, controlled by means of the control signal, to dispense the medical substance into the target tissue.

4. The electronic medical system of claim 1, wherein the implantable medical device comprises a second programmable control unit, operatively connected to the RF power receiver module, configured to manage the implantable medical device.

5. The electronic medical system of claim 4, wherein the implantable medical device further comprises a reference module operatively connected to both the RF power receiver module and the second programmable control unit, the reference module being configured to generate a reference voltage used by a pulse generator module within the RF power receiver module.

6. An electronic medical system, comprising:
an external RF power transmitter configured to emit a first energy signal via an electromagnetic coupling, said external RF power transmitter being configured to emit said first energy signal with a power no greater than 1 W;
an implantable medical device comprising:
at least one receiver antenna configured to receive said first energy signal via the electromagnetic coupling;
an RF power receiver module operatively connected to the at least one receiver antenna, the RF power receiver module being configured to extract a second energy signal having a power of at least 1 milliwatt (mW), the RF power receiver module being powered by said second energy signal, the RF power receiver module being configured to generate a control signal;
a power actuator module, operatively connected to the RF power receiver module, powered by said second energy signal, the power actuator module being configured to receive said control signal, the power actuator module being configured to deliver a medical treatment to at least a target tissue of a patient on a basis of said control signal; and
wherein the implantable medical device comprises a RF front end module, an impedance matching network, a voltage rectifier, the power actuator module, and a voltage protection and backscattering module; and
wherein the voltage protection and backscattering module is operatively connected to the at least one receiver antenna via the RF front end module, the voltage protection and backscattering module being operatively connected to the target tissue, the voltage protection and backscattering module being configured to transmit to the external RF power transmitter feedback information received from the target tissue.

7. The electronic medical system of claim 6, wherein the medical treatment is an electronic stimulation, the power actuator module comprising a pulse signal generator configured to apply electrical stimulation to the target tissue, controlled by means of the control signal, providing electrical stimulus to one or more electrodes connected to the target tissue.

8. The electronic medical system of claim 6, wherein the medical treatment is an action of a medical substance, the power actuator module comprising a pump, controlled by means of the control signal, to dispense the medical substance into the target tissue.

9. The electronic medical system of claim 6, wherein the implantable medical device further comprises a second communication interface module operatively connected to the RF power receiver module, said second communication interface module being configured to communicate data with the external RF power transmitter via a wireless link.

10. The electronic medical system of claim 9, wherein the implantable medical device comprises a second programmable control unit, operatively connected to the RF power receiver module, configured to manage the implantable medical device.

11. The electronic medical system of claim 10, wherein the implantable medical device further comprises a reference module operatively connected to both the RF power receiver module and the second programmable control unit, the reference module being configured to generate a reference voltage used by a pulse generator module within the RF power receiver module.

\* \* \* \* \*